(12) United States Patent
Chung et al.

(10) Patent No.: US 9,097,664 B2
(45) Date of Patent: *Aug. 4, 2015

(54) METHOD AND SYSTEM FOR CONCENTRATING PARTICLES FROM A SOLUTION

(71) Applicant: University of Washington, Seattle, WA (US)

(72) Inventors: Jae-Hyun Chung, Bellevue, WA (US); Woonhong Yeo, Seattle, WA (US); Kyong-Hoon Lee, Redmond, WA (US); Jeffrey W. Chamberlain, Seattle, WA (US); Gareth Fotouhi, Sonoma, CA (US); Shieng Liu, Bellevue, WA (US); Kie Seok Oh, Seattle, WA (US); Daniel M. Ratner, Seattle, WA (US); Dayong Gao, Bellevue, WA (US); Fong-Li Chou, Issaquah, WA (US)

(73) Assignee: University of Washington, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/106,357

(22) Filed: Dec. 13, 2013

(65) Prior Publication Data

US 2014/0251808 A1    Sep. 11, 2014

Related U.S. Application Data

(63) Continuation of application No. 12/480,627, filed on Jun. 8, 2009, now Pat. No. 8,632,669.

(60) Provisional application No. 61/059,708, filed on Jun. 6, 2008, provisional application No. 61/108,799, filed on Oct. 27, 2008.

(51) Int. Cl.
*G01N 27/447* (2006.01)
*G01N 1/40* (2006.01)
*G01N 33/569* (2006.01)

(52) U.S. Cl.
CPC ............ *G01N 27/44791* (2013.01); *G01N 1/40* (2013.01); *G01N 27/447* (2013.01); *G01N 33/569* (2013.01); *G01N 2001/4038* (2013.01)

(58) Field of Classification Search
CPC ...................... G01N 27/447; G01N 27/44791
USPC ................ 204/450, 547, 643, 600; 205/777.5
See application file for complete search history.

(56) References Cited

U.S. PATENT DOCUMENTS 6,280,590 B1    8/2001  Cheng
6,479,644 B1   11/2002  Bertling
(Continued)

FOREIGN PATENT DOCUMENTS

CN    1364940 A    8/2002
CN    1849181 A   10/2006
(Continued)

OTHER PUBLICATIONS

Kim et al. "Use of dielectrophoresis in the fabrication of an atomic force microscope tip with a carbon nanotube: experimental investigation," Nanotechnology 17 (20-06) 2937-2941.*

(Continued)

*Primary Examiner* — Alex Noguerola
(74) *Attorney, Agent, or Firm* — Christensen O'Connor Johnson Kindness PLLC

(57) ABSTRACT

Methods and systems are provided for concentrating particles (e.g., bacteria, viruses, cells, and nucleic acids) suspended in a liquid. Electric-field-induced forces urge the particles towards a first electrode immersed in the liquid. When the particles are in close proximity to (e.g., in contact with) the first electrode, the electrode is withdrawn from the liquid and capillary forces formed between the withdrawing electrode and the surface of the liquid immobilize the particles on the electrode. Upon withdrawal of the electrode from the liquid, the portion of the electrode previously immersed in the liquid has particles immobilized on its surface.

18 Claims, 20 Drawing Sheets

(56) References Cited

U.S. PATENT DOCUMENTS

| | | |
|---|---|---|
| 6,673,225 B1 | 1/2004 | Arnold |
| 7,014,743 B2 | 3/2006 | Zhou |
| 7,917,966 B2 * | 3/2011 | Kim et al. .................. 850/58 |
| 8,632,669 B2 * | 1/2014 | Chung et al. .................. 204/450 |
| 2002/0064795 A1 | 5/2002 | Hashimoto |
| 2003/0124572 A1 | 7/2003 | Umek |
| 2003/0159932 A1 | 8/2003 | Betts |
| 2004/0173378 A1 | 9/2004 | Zhou |
| 2005/0059105 A1 | 3/2005 | Alocilja |
| 2005/0070841 A1 | 3/2005 | Mathiesen |
| 2006/0169589 A1 | 8/2006 | Takagi |
| 2006/0213259 A1 | 9/2006 | Prinz |
| 2009/0211910 A1 * | 8/2009 | Hunt et al. .................. 204/547 |
| 2009/0223826 A1 * | 9/2009 | Kim et al. .................. 205/96 |

FOREIGN PATENT DOCUMENTS

| | | |
|---|---|---|
| CN | 101281202 A | 10/2008 |
| JP | 7-23796 A | 1/1995 |
| JP | 2000-515508 A | 11/2000 |
| JP | 2003-88383 A | 3/2003 |
| JP | 2006-61027 A | 3/2006 |
| JP | 2006-513048 A | 4/2006 |
| JP | 2006-246731 A | 9/2006 |
| JP | 2007-319035 A | 12/2007 |
| WO | 2004/052489 A2 | 6/2004 |

OTHER PUBLICATIONS

U.S. Appl. No. 61/031,523, filed Feb. 26, 2008.*
"Patch Clamp Micromanipulators: Burleigh PCS-6000®: The Piezo-Driven Advanced Positioning System for Ultimate Control," Lumen Dynamics, Mississauga, Canada, 4-page brochure, cited in an Office Action dated Jun. 18, 2013, in parent U.S. Appl. No. 12/480,627.
International Search Report mailed Feb. 17, 2010, issued in corresponding International Application No. PCT/US2009/046652, filed Jun. 8, 2009, 4 pages.
International Written Opinion mailed Feb. 17, 2010, issued in corresponding International Application No. PCT/US2009/046652, filed Jun. 8, 2009, 3 pages.
Japanese Office Action received Mar. 28, 2013, issued in corresponding Japanese Patent Application No. 2011-512751, filed Jun. 8, 2009, 3 pages.
Notification of the Second Office Action, mailed Feb. 28, 2013, issued in corresponding Chinese Application No. 200980127572.3, filed Jun. 8, 2009, 10 pages.
Notification of the Third Office Action, mailed Jun. 27, 2013, issued in corresponding Chinese Application No. 200980127572.3, filed Jun. 8, 2009, 12 pages.

* cited by examiner

```
                              SEQUENCE LISTING

<160> NUMBER OF SEQ ID NOS: 2

<210> SEQ ID NO 1
<211> LENGTH: 24
<212> TYPE: DNA
<213> ORGANISM: Mycobacterium tuberculosis

<400> SEQUENCE: 1
cagcgccgac agtcggcgct tgtg                                              24

<210> SEQ ID NO 2
<211> LENGTH: 24
<212> TYPE: DNA
<213> ORGANISM: Mycobacterium tuberculosis

<400> SEQUENCE: 2
cacaagcgcc gactgtcggc gctg                                              24
```

METHOD AND SYSTEM FOR CONCENTRATING PARTICLES FROM A SOLUTION

CROSS-REFERENCE TO RELATED APPLICATION

This application in a continuation of U.S. patent application Ser. No. 12/480,627, filed Jun. 8, 2009, which claims the benefit of U.S. Provisional Application No. 61/059,708, filed Jun. 6, 2008, and U.S. Provisional Application No. 61/108, 799, filed Oct. 27, 2008, each of which is incorporated herein by reference in its entirety.

STATEMENT OF GOVERNMENT LICENSE RIGHTS

This invention was made with Government support under grant number 0740525 awarded by National Science Foundation; and under grant number 200-2007-M-22794 awarded by the Center for Disease Control. The Government has certain rights in the invention.

STATEMENT REGARDING SEQUENCE LISTING

The sequence listing associated with this application is provided in text format in lieu of a paper copy and is hereby incorporated by reference into the specification. The name of the text file containing the sequence listing is 33312_Seq_Listing_Final.txt. The text file is 1 KB; was created on Jun. 8, 2009; and is being submitted via EFS-Web.

BACKGROUND

Tuberculosis (TB), one of the most widely spread diseases in the globe today, has infected one-third of the world's population. In 2006, 9.2 million new TB cases were reported, with 1.7 million related deaths, mostly in developing countries. In 2006, approximately 15,000 new TB cases were reported in the United States. Because a patient with active but untreated TB can infect on average between 10 and 15 people per year, the prompt diagnosis of new TB patients is essential to effectively control the disease.

Currently, there are multiple techniques for TB diagnosis. However, none of the available methods have a superior combination of low detection limits, analysis time, and cost. Those techniques with low detection limits are time consuming, while relatively fast tests have high detection limits and typically need to be verified eventually by a (slow) assay. Despite mature technologies for testing TB, improved detection methods are required to address the disease on a global scale.

Another analyte of interest is extracellular DNA, which is of great interest in the fields of disease diagnostics and environmental molecular biology. Unlike the genomic DNA in living cells, extracellular DNA is the free DNA released from dying cells. Thus, extracellular DNA circulating in body fluids can be used as an early indicator for various acute diseases such as cancer. For example, the concentration of extracellular DNA for a healthy person is about 30 ng/mL, but the concentration is increased to about 300 ng/mL for a cancer patient.

For environmental monitoring, extracellular DNA dissolved in lakes and soil is an indicator of environmental quality because the dissolved DNA is generated from cell lysis and excretion from living organisms.

Despite great interest, the study of extracellular DNA is hindered by the standard sample preparation methods currently utilized. The conventional method begins with filtering, centrifuging, and collecting DNA from a raw sample. Several hours are typically required for the sample preparation process, which can degrade and mutate extracellular DNA. As a result, the original information of extracellular DNA is partially or completely lost prior to analysis. Therefore, a rapid process that can concentrate extracellular DNA is very important for identifying pathogenic information.

The above examples of TB and extracellular DNA are scientifically significant analytes that are currently tested using methods that are slow, inefficient, and inadequate. An improved method for extracting particulate analytes, such as TB and DNA from a solution would provide a great benefit to global heath by improving the efficiency, cost, and accuracy of tests for diseases such as TB and cancer.

SUMMARY

In one aspect, a method is provided for concentrating a particle, comprising immersing a first electrode having a high aspect ratio in a liquid comprising a particle, wherein the first electrode comprises a shaft having a shaft latitudinal dimension and a distal end having a distal latitudinal dimension, wherein the distal latitudinal dimension is from one nanometer to one millimeter; urging the particle toward the first electrode by generating an electric-field-induced force using the first electrode; and immobilizing the particle on a surface of the first electrode with a capillary force formed between the first electrode and the liquid by withdrawing the first electrode from the liquid.

In another aspect, a particle concentrating system is provided, comprising a first electrode having a high aspect ratio, wherein the first electrode comprises a shaft having a shaft latitudinal dimension and a distal end having a distal latitudinal dimension, wherein the distal latitudinal dimension is from one nanometer to one millimeter a first liquid comprising a first particle; an actuator sized and configured to immerse and withdraw the first electrode from the first liquid such that a capillary force formed between the withdrawing first electrode and the first liquid immobilizes the first particle on a surface of the first electrode; and an electric signal generator sized and configured to generate an electrically induced force with the first electrode such that when the first electrode is immersed in the first liquid, the first particle is preferentially urged toward the first electrode.

In another aspect, a method is provided for concentrating a particle, comprising: immersing a first electrode having a high aspect ratio in a liquid comprising a particle, wherein the first electrode comprises a shaft having a shaft latitudinal dimension and a distal end having a distal latitudinal dimension, wherein the distal latitudinal dimension is from one nanometer to one millimeter; and urging the particle toward the first electrode by generating an electric-field-induced force using the first electrode.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1A:
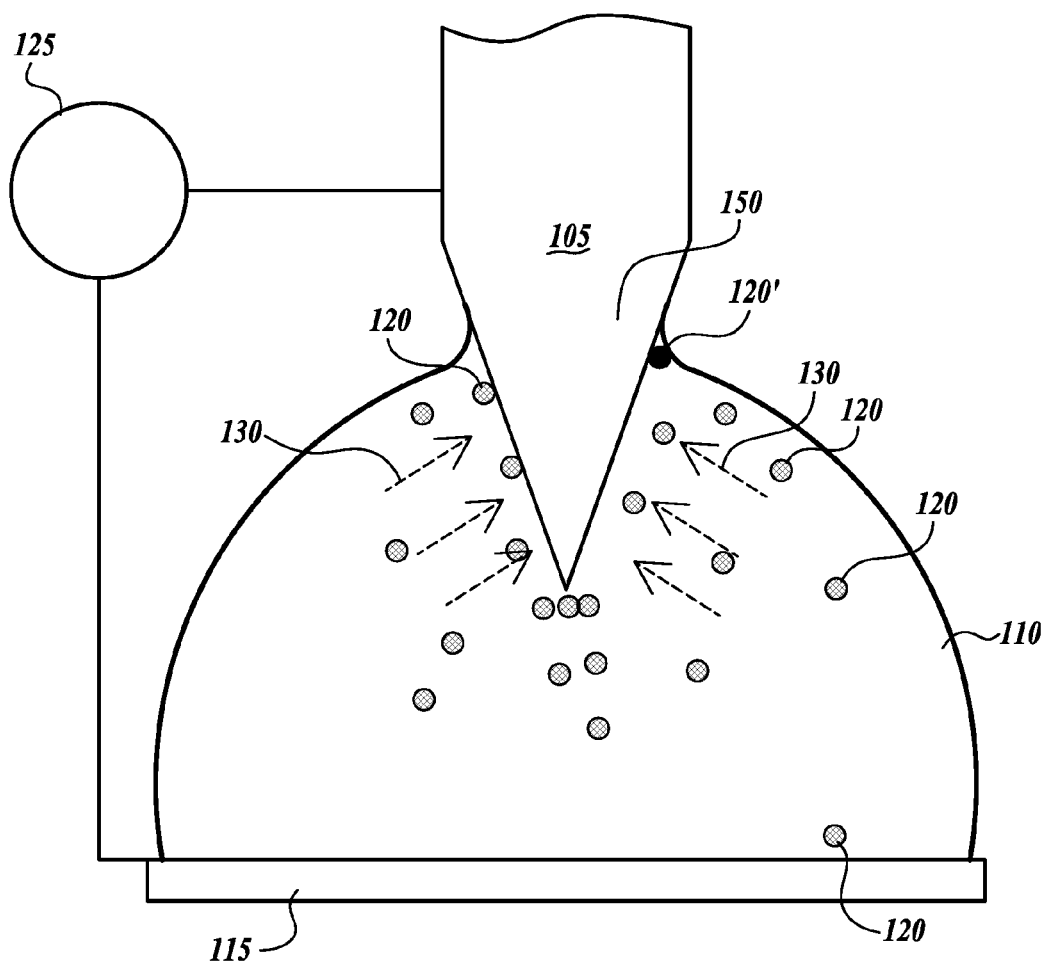
FIG. 1A is a diagrammatic illustration of a portion of a representative embodiment of the invention, including the substantially linear movement of particles in a liquid towards a first electrode by an electric-field-induced dielectrophoretic force generated by the first electrode.

In one aspect, a method is provided for concentrating a particle, comprising immersing a first electrode having a high aspect ratio in a liquid comprising a particle, wherein the first electrode comprises a shaft having a shaft latitudinal dimension and a distal end having a distal latitudinal dimension, wherein the distal latitudinal dimension is from one nanometer to one millimeter; urging the particle toward the first electrode by generating an electric-field-induced force using the first electrode; and immobilizing the particle on a surface of the first electrode with a capillary force formed between the first electrode and the liquid by withdrawing the first electrode from the liquid.

Methods and systems for concentrating particles (e.g., bacteria, viruses, cells, and nucleic acids) suspended in a liquid are provided. Electric-field-induced forces urge the particles towards a first electrode immersed in the liquid. When the particles are in close proximity to (e.g., in contact with) the first electrode, the electrode is withdrawn from the liquid and capillary forces formed between the withdrawing electrode and the surface of the liquid immobilize the particles on the electrode. Upon withdrawal of the electrode from the liquid, particles are immobilized on the portion of the electrode previously immersed in the liquid. Depending on the geometric shape of the electrode, the particles are immobilized on the distal tip, the sides, or both. The particles on the surface of the electrode are concentrated more densely on the electrode than in the solution, and thus analysis of the particles (e.g., by fluorescence spectroscopy) is improved.

In addition to concentrating particles for analysis, the concentrated particles can be further manipulated. For example, the particles on the electrode can be stored for future use (e.g., with cryogenic freezing), or introduced into a second liquid (e.g., in situ introduction of the particles into a cell).

As will be described in further detail below, the methods and systems disclosed herein provide a simple, fast, and inexpensive means for analyzing biological fluids for a variety of medically relevant analytes, such as bacteria (e.g., tuberculosis), viruses (e.g., HIV), cells (e.g., *drosophila* cells), and nucleic acids (e.g., DNA and RNA).

For example, the method of the invention has been demonstrated for detecting tuberculosis (TB) directly from human sputum in 10 minutes by concentrating and immobilizing TB bacteria on an electrode and analyzing the bacteria with fluorescence spectroscopy. The currently accepted method for detecting TB, the Ziehl-Neelsen smear test, typically requires up to three days to complete. Thus, in this exemplary embodiment, the invention provides dramatically improved detection of TB; additional embodiments provide similar capabilities for detection of other diseases.

The method begins by immersing a first electrode in a liquid comprising a particle. The liquid typically contains a plurality of particles and the particles are typically an analyte, such as a bacteria, virus, or other target molecule to be detected.

The first electrode is made from an electrically conductive material such as a metal, a doped semiconductor, or a conductive polymer. Metal-coated insulators are also useful in the method, as long as a sufficient electric field can be generated with the first electrode so as to generate an electric-field-induced force as described below.

As used herein, the term "aspect ratio" with reference to the first electrode means the ratio of a diameter of the first electrode (e.g., the distal tip diameter) to the length of first electrode immersed in the liquid. If an electrode is conical, the average diameter of the electrode provides an estimate of the diameter of the first electrode.

The first electrode has a high aspect ratio, so as to provide a relatively large surface area immersed within the liquid. For a high aspect ratio first electrode, the diameter of the distal tip is smaller than 1 mm and thus provides a relatively small area for generating a high-strength electric field during the method. For example, the high aspect ratio of the first electrode, in an exemplary embodiment, provides a concentrated electric field sufficient to attract DNA to the electrode using DEP. In one embodiment, a high aspect ration has a diameter: length ratio of from 1:1 to 1:100.

In one embodiment, the first electrode includes a tip, wherein the tip of the first electrode is the distal end of the first electrode and terminates in a single point. The first electrode tip may be conical, rounded, or truncated. In one embodiment, the distal end is truncated and has no tip terminating in a single point.

The first electrode includes a shaft having a shaft latitudinal dimension and a distal tip having a distal latitudinal dimension. For a conical tip, the distal latitudinal dimension is smaller than the shaft latitudinal dimension. The latitudinal dimensions are equal for a cylindrical first electrode with no tip.

The shape of the first electrode can be modified to suit a particular application. The geometry of the tip will determine the position on the first electrode where particles are preferentially immobilized through the method of the invention. For example, a cylindrical first electrode having a truncated distal end will tend to concentrate particles on the sides of the cylinder as opposed to the truncated distal end of the cylinder.

The terms "nanotip" and "microtip" are used herein to describe a first electrode having a diameter less than about one micron and greater than about one micron, respectively.

The liquid is any liquid capable of suspending, or solvating, the particles. Representative liquids include water, organic solvents, and ionic solvents. The liquid of the method can be a solution or a suspension and representative liquids include biological fluids such as blood, sputum, mucus, and saliva. Biological fluids, in particular, are typically highly complex and contain numerous particles including bacteria, cells, proteins, DNA, and other bodies. In one embodiment of the invention, the first electrode is immersed directly into a biological fluid extracted from a living being, such as a blood sample, mucus sample, saliva sample, or sputum sample. A particular analyte particle, such as tuberculosis bacteria, is concentrated and immobilized on the first electrode using the method of the invention. In one embodiment, the biological fluid is processed between extraction from the living being and testing. Such processing may include acid and/or base treatment, dilution, chemical processing, heating/cooling, or other processing steps necessary to prepare the sample for use in the method. One benefit, however, of the method compared to some known methods for testing, for example, tuberculosis bacteria, is that little or no preparation of biological fluids is necessary for performing the method of the invention, whereas extensive processing of samples is required for known methods.

The first electrode is immersed in the liquid so as to bring the electrode into proximity with the particles to be immobilized. The first electrode is entirely, or partially, immersed in the liquid. The method continues with the generation of an electric-field-induced force by the first electrode that urges the particles toward the first electrode surface. The electric-field-induced force is an electrokinetic or dielectrokinetic force extending from the first electrode and acting on the particles. Representative electric-field-induced forces include dielectrophoresis, electroosmotic flow, electrophoresis, and combinations thereof. In one embodiment, the electric-field-induced force is generated between the first electrode and a second electrode in contact with the liquid. The electric-field-induced forces typically require a first electrode and a second electrode to generate the force. The first electrode is in contact with the liquid because it is immersed in the liquid. The second electrode is also in contact with the liquid and can be an electrode inserted into the liquid or can be a support for the liquid, as will be discussed further with regard to FIGS. 1A-3.

The latitudinal cross-section of the first electrode can have any shape. Representative shapes include circular, triangular, and square cross sections. Conical electrodes are particularly useful because common micro- and nano-scale fabrication methods result useful for making first electrodes of the invention result in conical-shaped electrodes (e.g., cutting mesoscale wire to a point or assembling nanowires into a conical structure). Representative first electrodes also include geometric-shaped cross-sections (e.g., square) that then truncate in a tapered distal end ("tip"), such as a circular cross-section wire that truncates in a conical or hemi-sphere tip.

The electric-field-induced forces useful in the method of the invention are known to those of skill in the art and will only be briefly described herein. Dielectrophoresis (DEP) is a dielectric force wherein an induced dipole in the particle results in the attraction or repulsion of the particle to areas of high or low electric potential, based on whether the DEP effect is positive DEP or negative DEP. An alternating current is typically used to drive the DEP force. In the embodiments described herein, positive DEP is typically utilized to attract particles to the surface of the first electrode.

Electroosmosis generates flow in the liquid that transports particles to the first electrode through a drag force that results in particle concentration. When an AC field is applied to the first electrode, an ion layer forms on the surface of the first electrode. The sign of the charge of the electrodes (and the resulting double layer) changes according to the alternation of the potential. In such a case, an electrostatic force of charged ions is generated in the tangential direction to the surface, which induces AC electroosmotic flow. The electric field strength decreases with increasing distance from the end of the first electrode, and the flow speed is maximal at the electrode distal end and decreases rapidly further up the shaft of the electrode. Due to the non-uniform flow speeds resulting from field strength on the first electrode, vortices are produced in the liquid (that concentrate particles in the vicinity of the first electrode).

FIG. 1A illustrates a diagrammatic view of a representative embodiment of the invention where a first electrode 105 is immersed in a liquid 110 supported by a second electrode 115. A plurality of particles 120 are suspended in the liquid 110. An electrical signal generator 125 is operatively connected to the first electrode 105 and the second electrode 115 to apply an AC and/or DC signal across the electrodes 105 and 115. Depending on the shapes of the electrodes 105 and 115, the applied signal from the electrical signal generator 125, the electric/dielectric properties of the particles 120, and the electric/dielectric properties of the liquid 110, several different electric-field-induced forces can be generated to manipulate the particles 120. FIG. 1A illustrates particles 120 influenced by DEP such that the particles 120 are urged linearly toward the first electrode 105 upon application of an electric field. The arrows 130 indicate the direction of the force on the particles 120 and the particles throughout the liquid are generally urged in the direction of the first electrode 105.

Figure 2:
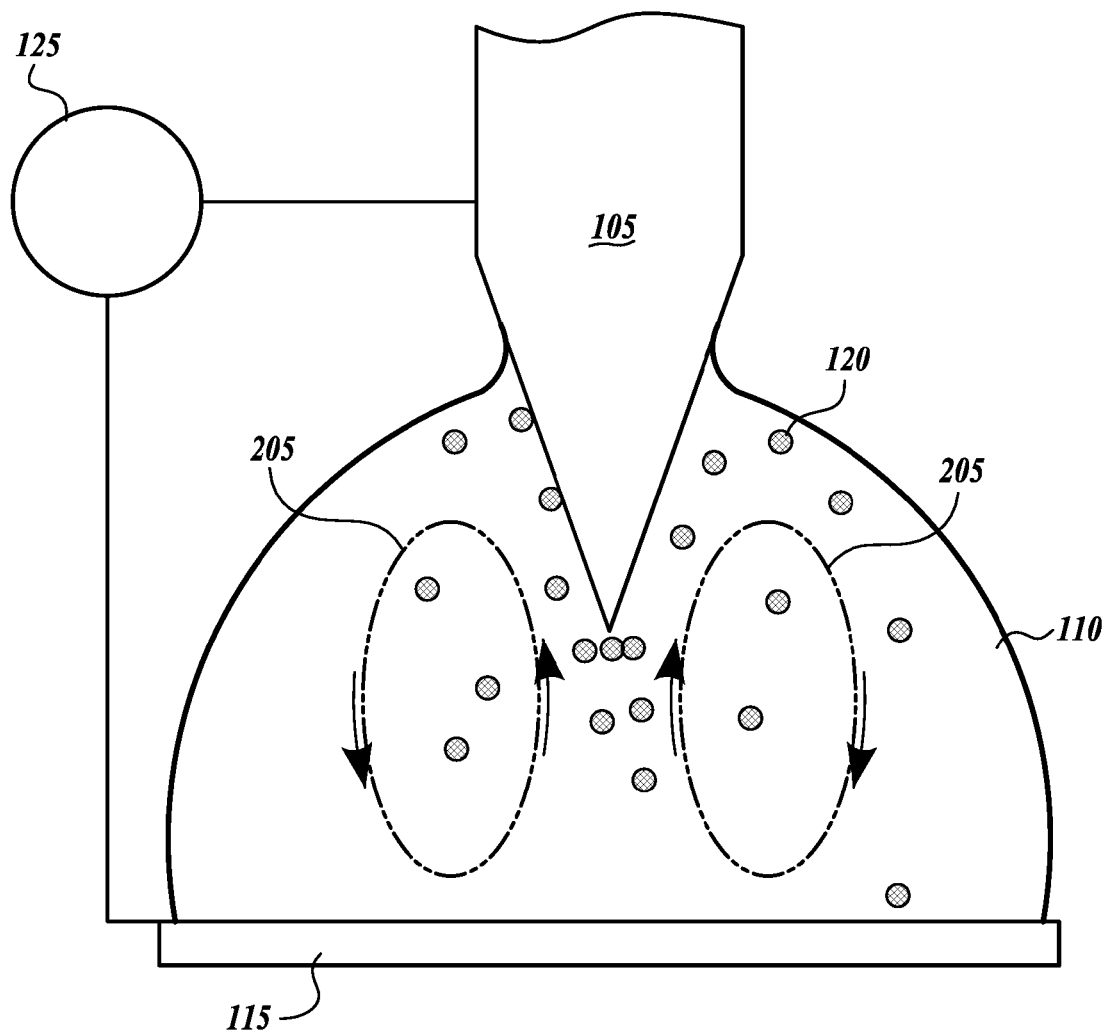
FIG. 2 is a diagrammatic illustration of a portion of a representative embodiment of the invention, including the circulating movement of particles in a liquid towards a first electrode by an electric-field-induced electroosmotic force.

FIG. 2 is a diagrammatic view similar to that of FIG. 1A, with only the electric-field-induced force changing between FIG. 1A and FIG. 2. In FIG. 2, the electric field generated by the electrical signal generator 125 between the first electrode 105 and second electrode 115 results in electroosmotic flow, illustrated as oval circles 205 indicating that the electric field generates flow patterns within the liquid 110 creating a circular circling pattern within the liquid 110. Particles 120 are influenced by the electroosmotic flow 205 and some particles 120 are preferentially urged toward the first electrode 105.

Figure 3:
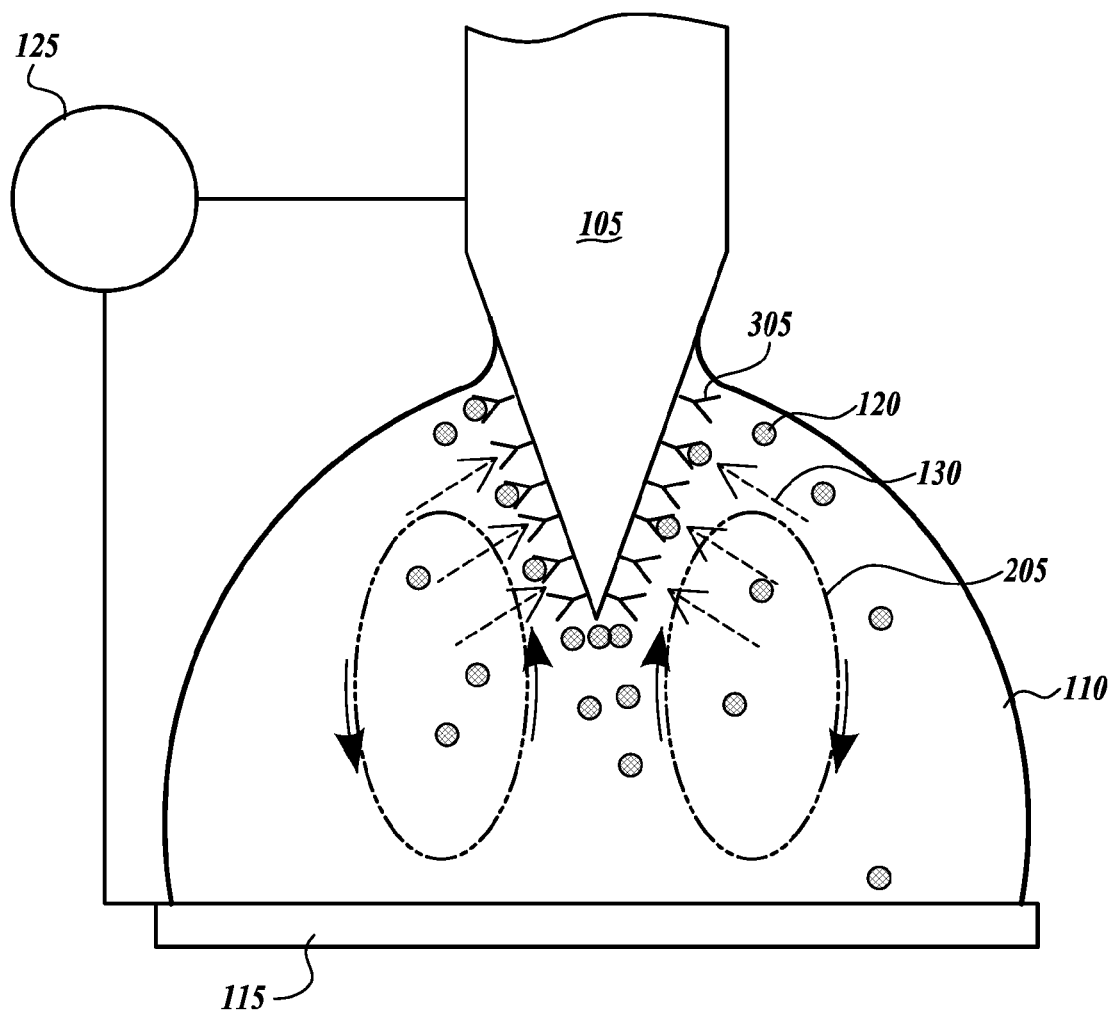
FIG. 3 is a diagrammatic illustration of a portion of a representative embodiment of the invention, including the combination of dielectrophoretic and electroosmotic forces on particles in a liquid urging the particles towards a first electrode comprising first binding partners capable of binding to second binding partners attached to the particles.

FIG. 3 illustrates a system similar to those illustrated in FIGS. 1A and 2. FIG. 3 illustrates both electroosmotic flow 205 and DEP 130 and also includes a layer of first binding partners 305 coating the surface of the first electrode 105. The first binding partners 305 preferentially bind to second binding partners that are attached to the particles 120. Thus, three forces are in effect in the system illustrated in FIG. 3, including electroosmotic flow 205 circulating the particles 120 within the liquid 110; DEP 130 preferentially urging the particles 120 toward the first electrode 105; and first binding partners 305, attached to the first electrode 105, preferentially binding the second binding partners attached to the particles 120. The resulting forces culminate in the movement of particles 120 through the liquid 110 toward the first electrode 105 upon the surface of which the particles 120 are concentrated.

The method disclosed herein continues with the step of immobilizing the analyte on the surface of the first electrode using the capillary force formed between a first electrode and the liquid by withdrawing a first electrode from the liquid.

Figure 1B:
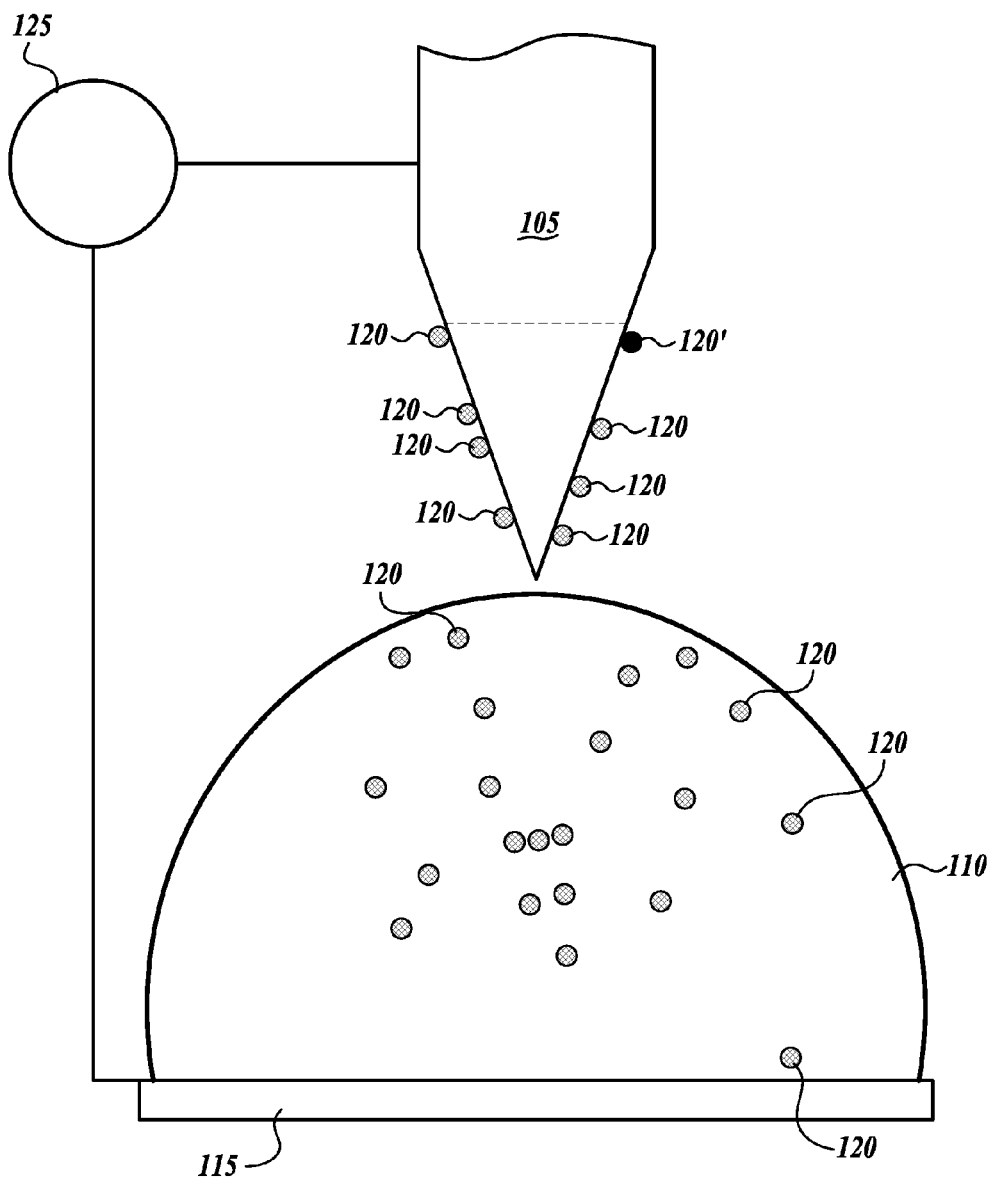
FIG. 1B is a diagrammatic illustration of a portion of the representative embodiment of the invention illustrated in FIG. 1A, wherein the first electrode is retracted from the liquid and has particles concentrated on its surface as a result of capillary forces immobilizing particles from the liquid that were attracted to the first electrode through electric-field-induced dielectrophoretic forces.

FIG. 1B illustrates a diagrammatic representation of the embodiment illustrated in FIG. 1A wherein the first electrode 105 has been retracted from the liquid 110 and the capillary action at the interface between the liquid 110 and the first electrode 105 immobilizes the particles trapped at that interface along the surface of the retracting first electrode 105. For example, particle 120' is illustrated in FIG. 1A at the interface between the first electrode 105 and the liquid 110 where the surface tension is illustrated in an exaggerated manner for the purpose of clarity. As the first electrode 105 withdraws from the liquid 110, the surface tension at the interface immobilizes the particles 120 adjacent to the first electrode 105 on the surface of the first electrode 105. FIG. 1B illustrates particle 120' and other particles 120 immobilized on the surface of the retracted first electrode 105.

The particles are immobilized on the surface of the first electrode upon withdrawal from the liquid. Prior to withdrawal from the liquid, the electric-field-induced forces and, optionally, the binding partner interactions, urge the particles into close proximity to the first electrode and, upon withdrawal, that proximity to the electrode combined with the capillary forces at the interface between the electrode and the liquid and the ambient atmosphere (solid-liquid-gas boundary), results in a force on the particles toward the surface of the first electrode. Once the particles are immobilized on the electrode, upon withdrawal from the liquid, a variety of forces act to keep the particles immobilized on the surface of the first electrode, including static electric forces, capillary forces, chemical bonding, and active electrical forces (e.g., the electric signal continues to be passed through the first electrode).

The speed of withdrawal of the electrode from the liquid can affect the size and number of particles immobilized on the surface of the first electrode. The withdrawal speed ranges from 1 μm/sec to 10 mm/sec. Slow withdrawal speeds are used to precisely control capillary action, which helps determine the size and number of particles captured. Fast withdrawal speeds are useful for devices that do not require precision operation (e.g., portable and/or disposable devices).

The method is useful for immobilizing particles smaller than the latitudinal dimension (e.g., diameter) of the first electrode at the solid-liquid-gas boundary. The balance of the forces for immobilizing particles on the first electrode is typically such that diameter of particles (assuming spherical particles) immobilized on the surface of the first electrode are smaller than the diameter of the first electrode (assuming a conical or cylindrical first electrode shape).

For a conical electrode 105, as illustrated in FIGS. 1A-3, the diameter of the tip of the first electrode varies through the length of the conical portion of the first electrode. As illustrated in FIGS. 1A and 1B, line 150 represents a latitudinal diameter of the conical first electrode at a particular position. The particles 120 immobilized onto a first electrode from the liquid will all be smaller in diameter than the diameter of the first electrode at line 150. The diameter gradient of the conical first electrode 105 illustrated in FIGS. 1A and 1B leads to the possibility that a gradient of maximum particle sizes will result from the use of such a first electrode 105 shape in a liquid 110 containing multiple particle sizes. For a narrow maximum particle size distribution, cylindrical first electrodes can be used.

Spherical particles are not required for the immobilization of the method of the invention to occur. It is convenient to use spheres for the purpose of representing particles, such as in FIGS. 1A-3, and for describing particles (e.g., particles having "a diameter"). However, spherical particles rarely occur at the micro- and nanoscales other than specifically formed micro- and nanospheres (e.g., polymer or inorganic nanospheres). In one embodiment, at least one dimension of the particle is smaller than the latitudinal diameter of the first electrode such that the combined forces of the electrically induced force, the size of the first electrode, and the capillary force combine to immobilize the particle on the surface of the first electrode.

In one embodiment, the particle is selected from the group consisting of an organic particle, an inorganic particle, a virus, a bacteria, a nucleic acid, a cell, and a protein. Other particles, including biological particles, not recited herein, are also compatible with the methods described herein.

In one embodiment, the virus is selected from the group consisting of coxsackievirus, hepatitis A virus, poliovirus, epstein-barr virus, herpes simplex, type 1, herpes simplex, type 2, human cytomegalovirus, human herpes virus, type 8, varicella-zoster virus, hepatitis B virus, hepatitis C virus, yellow fever virus, dengue virus, a flavivirus, human immunodeficiency virus (HIV), influenza virus, measles virus, mumps virus, parainfluenza virus, respiratory syncytial virus, papillomavirus, rabies virus, Rubella virus, human papillomavirus (HPV), ebola, marburg, hanta, reovirus, respiratory syncitial virus, avian flu virus, and West Nile virus. In one embodiment, the bacteria is selected from the group consisting of tuberculosis, *E. coli, staphylococcus aureus*, methicillin resistant *staphylococcus aureus* (MRSA), *salmonella*, and *pseudomonasis aeruginosa*. In one embodiment, the cell is a *drosophila* cell.

In one embodiment, the latitudinal dimension of the first electrode is less than 1 mm. In one embodiment, the latitudinal dimension of the first electrode is greater than 1 nm. In one embodiment, the latitudinal dimension of the first electrode is from 1 nm to 1 mm. As described above, particular first electrode shapes, such as conical electrodes, have varying latitudinal dimensions and the range of dimensions of this embodiment refers to the smallest measured latitudinal dimension, i.e., the distal tip of the electrode.

In one embodiment, the first electrode is at least partially coated with a surface coating. The first electrode can be coated for several purposes, including providing a buffer between the electrode material and the particles and/or the liquid; functionalizing the first electrode to selectively bind to particles; and functionalizing the first electrode to selectively repel particular types of particles (e.g., particles not desired for immobilization).

In one embodiment, the surface coating is either a monolayer or a polymer layer. Monolayers, such as self-assembled monolayers (SAM), are known to provide a route to functionalize surfaces through grafting particular molecular species to the surface. For example, the bond between thiol and gold is particularly well known to those of skill in the art and, thus, a gold first electrode can be functionalized with thiol-containing molecules to produce a gold first electrode having surface properties ranging from hydrophobic to hydrophilic and, additionally, customized chemical functionalities.

Polymer layers can also be used to coat the first electrode. In one embodiment, the polymer is a polysiloxane. An exemplary polysiloxane is polydimethylsiloxane (PDMS), is used as a buffer between the conductive material of the first electrode and the particles and liquid to preserve the integrity of the first electrode material. In an exemplary embodiment, the electrode is fabricated from a hybrid material of silicon carbide (SiC) nanowires and carbon nanotubes (CNT). The polymer protects the first electrode from degradation due to exposure to the liquid and also prevents nonspecific binding between particles such as DNA and the CNTs of the first electrode.

The surface coating at least partially coats the first electrode and, typically, the entire electrode is coated with the coating. However, selectively coating only portions of the first electrode may be utilized to direct particles toward or away from the portions of the first electrode that are coated or uncoated.

In one embodiment, the surface coating enhances the immobilization of the particle on the first electrode. The enhancement of the immobilization produced by the coating can be through any mechanism known to those of skill in the art. Particularly, by providing a hydrophobic or hydrophilic coating that preferentially binds particles having similar hydrophobic or hydrophilic character (e.g., a fluorinated alkane coating on the first electrode will preferentially bind to particles having hydrophobic character through a hydrophobic-hydrophobic interaction).

In one embodiment, the surface coating includes a first binding partner and the particle includes a second binding partner capable of binding to the first binding partner. The utilization of such binding partners provides binding between the first electrode and the particles when the particles are urged into close proximity to the first electrode through the use of electric-field-induced forces in the liquid. Binding partners are known to those of skill in the art and include chemical binding partners, antibody-antigen partners, nucleic acid binding (e.g., DNA and/or RNA), enzyme-substrate binding, receptor-ligand binding, nucleic acid-protein binding, and cellular binding (e.g., a cell, cell membrane, or organelle binding to a ligand for the cell, cell membrane, or organelle). Several exemplary embodiments of the binding of a first binding partner to a second binding partner in the method of the invention are provided below.

Upon immobilization of particles on the first electrode, several optional additional steps are provided for further processing of the concentrated particles, including analysis, storage, and release of the immobilized particles. In one embodiment, the method includes analyzing the particles immobilized on the surface of the first electrode.

Analysis can occur prior to immobilization, during immobilization, or after immobilization of the particles. Representative analytical techniques include techniques that occur while the first electrode is immersed (e.g., resistance detection), and other techniques are performed out of solution. Representative analysis techniques include electrical, mechanical, optical, and surface-imaging techniques and combinations thereof. In one embodiment, optical analysis includes the steps of attaching a luminescent compound (e.g., a fluorescent tag) to the particle (e.g., a DNA molecule) to provide a luminescent particle and detecting luminescence from the luminescent particle using fluorescence microscopy and/or fluorescence spectroscopy.

The immobilized particles can be immersed in a second liquid containing compounds that will interact with the immobilized particles to produce a particular effect, such as fluorescence. For example, DNA immobilized on an electrode can be immersed into a solution containing a molecule that fluoresces when hybridized with DNA. Upon hybridization with DNA, the DNA is detectable by fluorescence spectroscopy.

Representative techniques for electrical detection of analyte particles include techniques for measuring capacitance, resistance, conductance, impedance, and combinations thereof.

The method also provides for storing the first electrode to preserve the immobilized particles. In a representative embodiment, storing the first electrode includes cryogenic freezing to preserve the immobilized particles. Cryogenic freezing optionally includes immersing the immobilized particles in a cryopreservative (e.g., DMSO) prior to freezing. The stored particles may be preserved for future analysis using the techniques described above, or may be further manipulated at a later time.

In one embodiment, the method also includes the releasing of immobilized particles, such as releasing the particles from the first electrode into a solution providing enrichment of such a solution with the previously immobilized particles. Releasing the immobilized particles can include releasing the particles into a body selected from the group including a cell, a virus, and a bacteria. As will be described further below, the method can be used to selectively concentrate one type of particle, such as DNA, from one solution, such as a human blood sample, and withdraw the concentrated DNA on a first electrode from the blood sample and insert the DNA into a second environment (e.g., a cell), and release the immobilized DNA into the cell to provide a DNA-enriched second sample. This selective attachment, concentration, and release sequence can be performed using any of the particles described herein and, thus, molecular and nanoscale fabrication can be achieved through the immobilizing and releasing of selected particles to form a desired complex.

Immobilization and release can be effected through manipulation of thermal energy, chemical energy, electric energy, mechanical energy, or combinations thereof.

In one embodiment, the method includes immobilizing a relatively large particle (e.g., a cell) on a microtip and using a nanotip to immobilize relatively small particles from inside the larger particle (e.g., DNA).

In one embodiment, generating the electric-field-induced force includes orienting a surface coating. Particularly, if the surface coating is a monolayer of molecules or a thin layer of polymer molecules, the electric field providing the electric-field-induced force may tend to align the molecules of the surface coating—for example, along the electric field lines—and this alignment can assist in the binding between first binding partners and second binding partners by providing an oriented and aligned surface for attracting the binding partners attached to particles in the liquid.

Figure 4A:
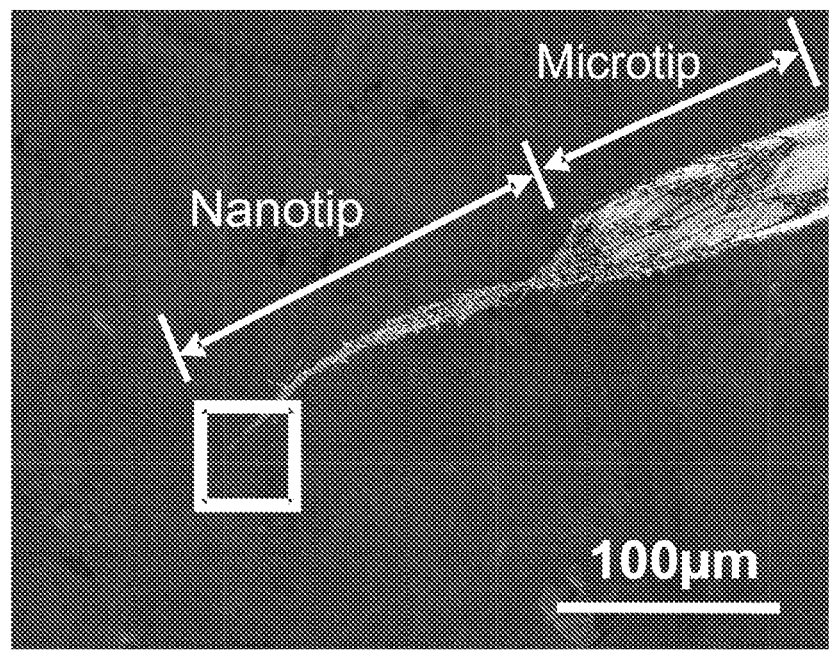
FIGS. 4A and 4B are micrographs of a representative first electrode made from silicon carbide and carbon nanotubes useful in the invention.
Figure 4B:
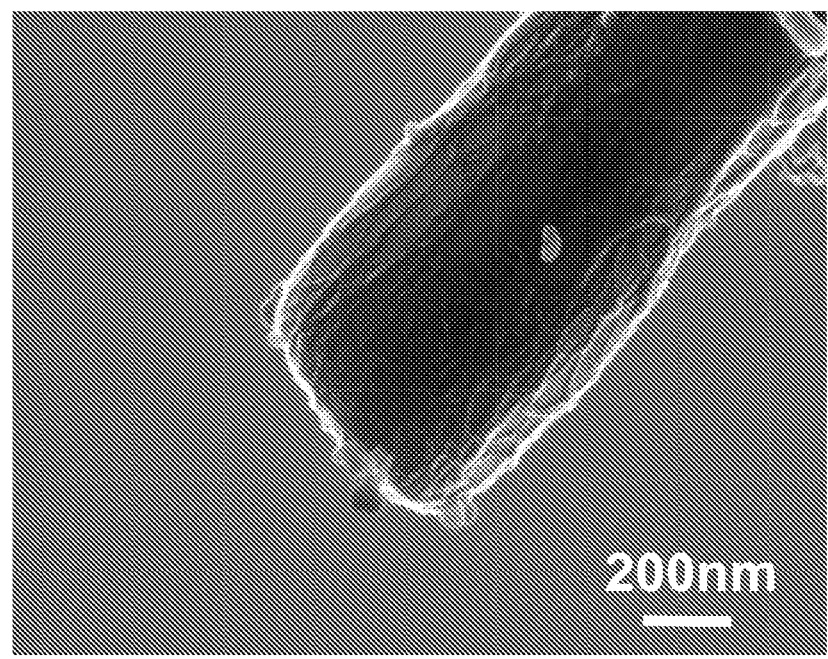
Figure 4C:
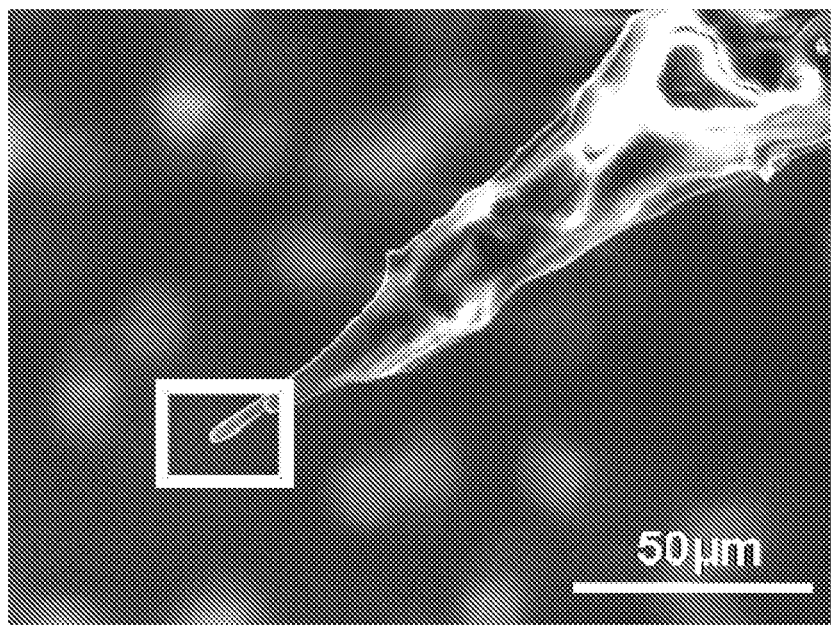
FIGS. 4C and 4D are micrographs of a polymer-coated first electrode useful in the invention.
Figure 4D:
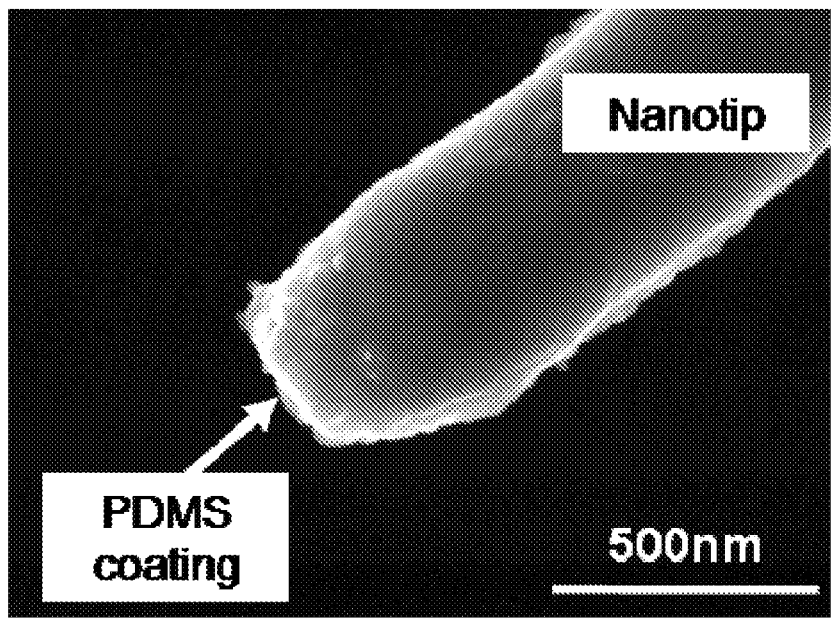

In one embodiment, the first electrode is comprised of a hybrid material of silicon carbide nanowires and carbon nanotubes (CNT/SiC) formed by methods described in U.S. Patent Application No. 61/108,799, incorporated herein by reference in its entirety. Briefly, the hybrid material is fabricated from a micron-sized tip of a metal material, such as gold-coated tungsten. The combined carbon nanotubes and silicon carbide wires are dispersed in separate containers using sonication for several hours. The solutions are combined and sonicated for one hour prior to use. The microtip is inserted into the combined CNT/SiC solution and an AC potential is applied to the microtip prior to withdrawing the microtip at a speed of about 10 μm per second, which results in the creation of bundles of carbon nanotubes adhered to, and joining together, the silicon carbide nanowires, as illustrated in the micrographs of FIG. 4A and FIG. 4B. PDMS-coated CNT/SiC electrodes are illustrated in FIGS. 4C and 4D.

The method also provides for a multiplexed version of the single first electrode concentrator described above. In this embodiment, the method further includes immersing a third electrode having a high aspect ratio in the liquid comprising the particles; generating an electric-field-induced force using the third electrode such that the particles in the liquid are preferentially urged toward the third electrode; and withdrawing the third electrode from the liquid such that a capillary force formed between the withdrawing third electrode and the liquid immobilizes the particles on the surface of the third electrode. The third electrode is analogous to the first electrode in the previously-described embodiments. A fourth electrode can optionally be introduced into the method of this embodiment such that the first electrode and second electrode pair to generate one electric-field-induced force in the liquid and the third and fourth electrodes pair to form a separate electric-field-induced force in the liquid. In an alternative embodiment, the first electrode and third electrode are immersed in separate liquid bodies (e.g., the first electrode is in a first liquid and the third electrode is in a second liquid) wherein each liquid may comprise the same or different particles. Thus, several electrodes may be used to concentrate particles from a single liquid body or from multiple liquid bodies, such as in parallel assays for drug candidate screenings or biological testing. Additionally, through surface functionalization of an electrode (e.g., the first electrode), multiple species can be specifically immobilized and detected and/or stored simultaneously, which can enhance throughput and reduce detection cost and time.

In another aspect, the invention provides a particle concentrating system. In one embodiment, the particle concentrating system includes a first electrode having a high aspect ratio and a latitudinal dimension; a first liquid comprising a first particle having a latitudinal dimension less than the latitudinal dimension of the first electrode; an actuator sized and configured to immerse and withdraw the first electrode from the first liquid such that a capillary force formed between the withdrawing first electrode and the first liquid immobilizes the first particle on a surface of the first electrode; and an electric signal generator sized and configured to generate an electrically-induced force with the first electrode such that when the first electrode is immersed in the first liquid, the first particle is preferentially urged toward the first electrode.

The particle concentrating system described herein has been described above with reference to the method of the invention and such aspects as the electrodes, liquids, and particles are applicable to both the method and the system.

The actuator sized and configured to immerse and withdraw the first electrode from the liquid can be any actuator known to those of skill in the art and, in a preferred embodiment, the actuator is a mechanical actuator such as a piezoelectric actuator or a manually positionable actuator (e.g., a micromanipulator). The actuator has a movement range capable of extending a portion of the first electrode into the liquid and retrieving the entire first electrode from the liquid such that the immobilized particles can be further manipulated or analyzed.

The electric signal generator can be any signal generator known to those of skill in the art, such as those capable of delivering an AC and/or DC signal to the first and second electrodes of the system.

Systems including further pairs of electrodes are also contemplated and the electrical signal and actuation of each pair of electrodes can be controlled either independently of the other electrode pairs or in conjunction with the other electrode pairs.

In another aspect, a method is provided for concentrating a particle, comprising: immersing a first electrode having a high aspect ratio in a liquid comprising a particle, wherein the first electrode comprises a shaft having a shaft latitudinal dimension and a distal end having a distal latitudinal dimension, wherein the distal latitudinal dimension is from one nanometer to one millimeter; and urging the particle toward the first electrode by generating an electric-field-induced force using the first electrode. The various details of this embodiment have been described herein (e.g., the particles, electrode materials, and liquids) with regard to the above aspects and embodiments.

In one embodiment the particles are immobilized on the surface of the first electrode using the electric field induced force, as described above. Immobilization optionally includes binding interactions as described above. In this embodiment, electrical detection (e.g., resistance measurement) is useful for detecting binding events at the surface of the first electrode, as described herein.

Polymer Nanosphere Immobilization and Size Selectivity

Figure 5A:
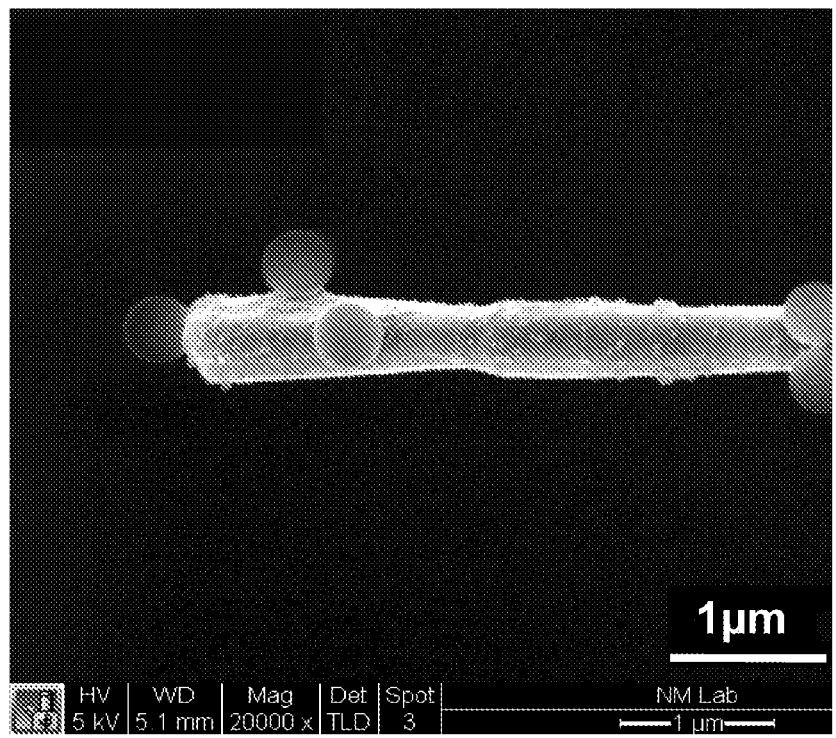
FIGS. 5A-5C are micrographs of a representative first electrode made from silicon carbide and carbon nanotubes after performing the method of the invention and having polymer particles immobilized on its surface.
Figure 5B:
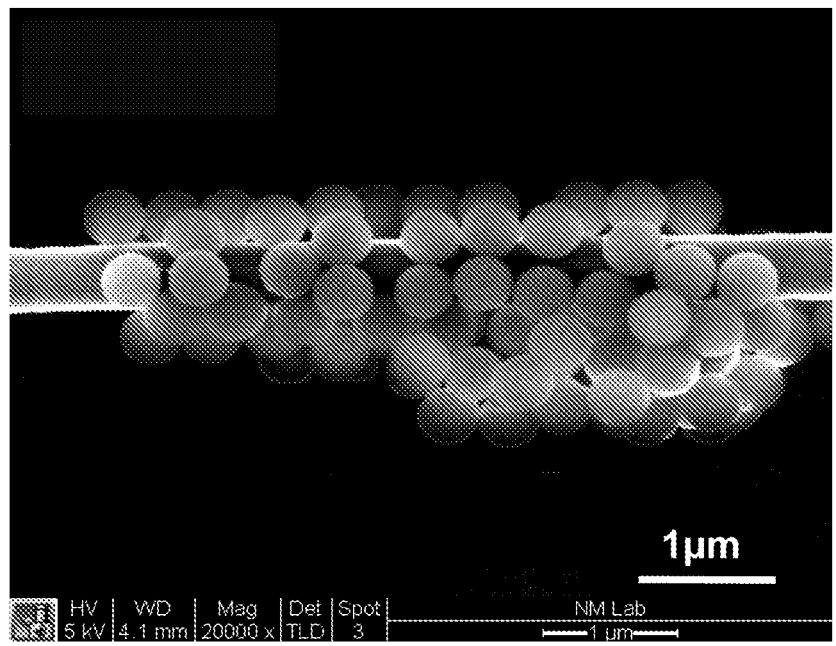
Figure 5C:
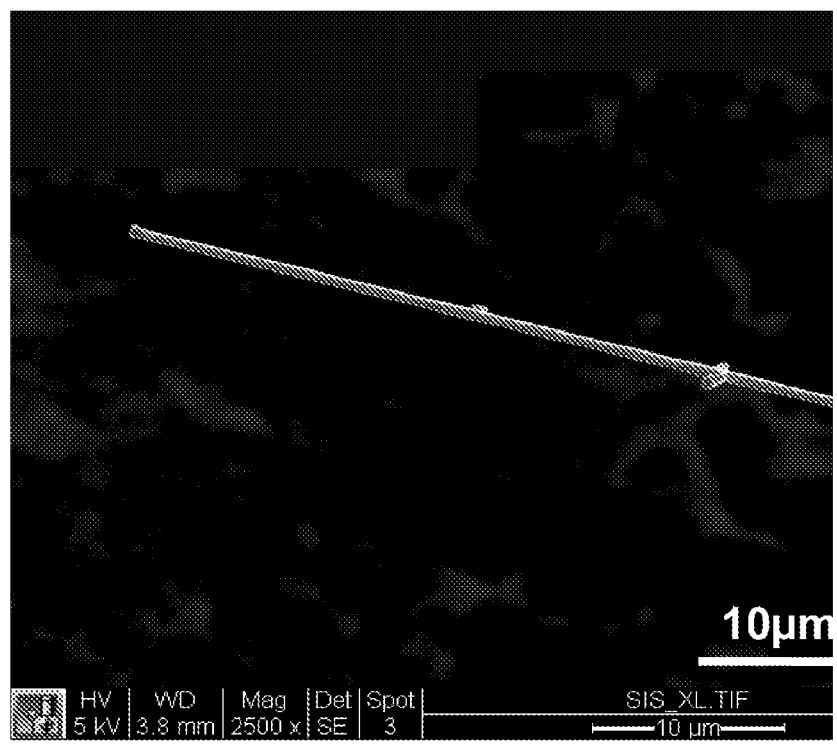

In this exemplary embodiment, dielectrophoresis and capillary forces are used to immobilize polystyrene nanospheres on an electrode. A CNT/SiC electrode ("nanotip") was immersed in an aqueous solution containing nanospheres, supported as a 2 μL droplet within a tungsten coil, which acted as a second electrode. An AC potential of 20 $V_{pp}$ at 10 kHz was applied between the electrodes and polystyrene spheres in the vicinity of the nanotip were attracted to the nanotip by the generated DEP force. The spheres were immobilized on the nanotip upon withdrawal from the solution at a speed of 8 μm/s, as illustrated in FIG. 5A (450 nm spheres; 525 nm tip); FIG. 5B (475 nm spheres; 515 nm tip); and FIG. 5C (100 nm spheres captured on a 600 nm tip from a mixture of 100 nm spheres and 6 micron spheres). FIG. 5C illustrate the size selectivity of the invention: spheres smaller than the tip diameter were immobilized, while larger spheres were not.

When an electrode is surrounded with a cluster of spheres, a multiple-particle interaction may occur and the spheres are immobilized onto the side of the tip as shown in FIG. 5B. The cluster formation around an electrode arises during the nanosphere immobilization process because the spheres are urged to the solid-liquid-gas interface by capillary action. The delivery of spheres to the interface can be generated by the DEP force in conjunction with evaporation of liquid and the compressive force due to capillary action.

Other than the geometric- and multiple-particle-interaction effects, the surface properties of an electrode and electric field effects (e.g. electro-wetting) will affect the surface tension and, thus, the balance of forces acting to immobilize the particles. Additionally, molecular interaction forces (e.g. van der Waals force) are also present. Thus, there are several variables that affect the conditions leading to particle immobilization at the air-liquid-solid interface, and each system of particles, electrically-induced forces, liquids, and ambient conditions will produce a unique set of parameters for immobilizing the target particles. Experimental conditions can be optimized to preferentially immobilize the target particles of interest.

DNA Immobilization

Figure 6A:
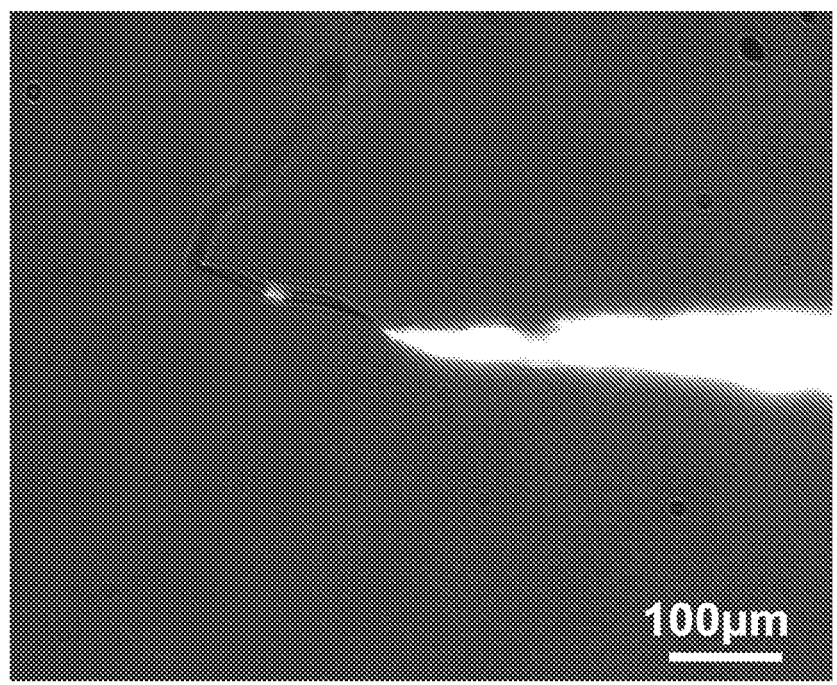
FIGS. 6A-6C are micrographs of a representative first electrode of the invention having DNA immobilized on its surface.
Figure 6B:
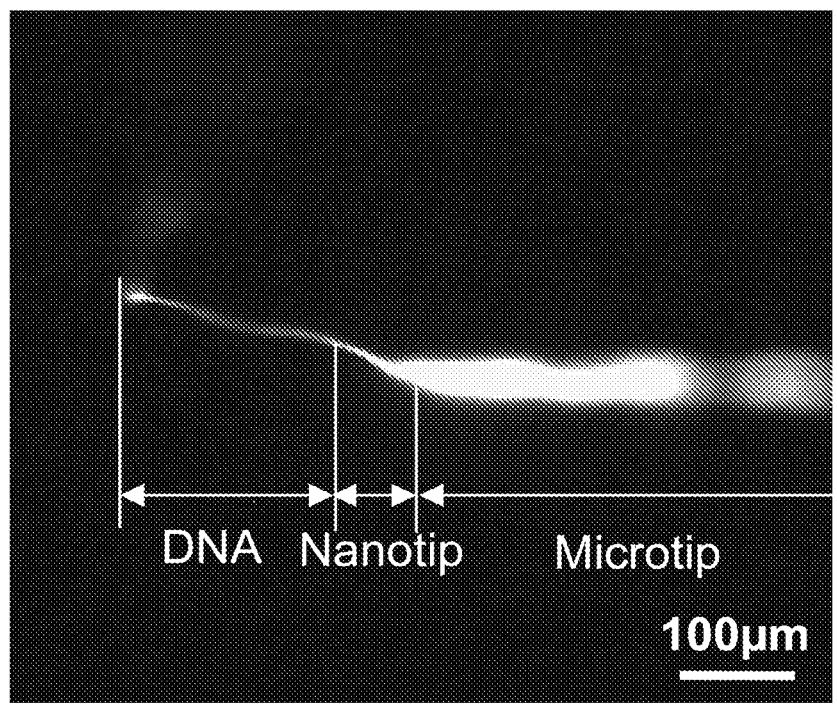
Figure 6C:
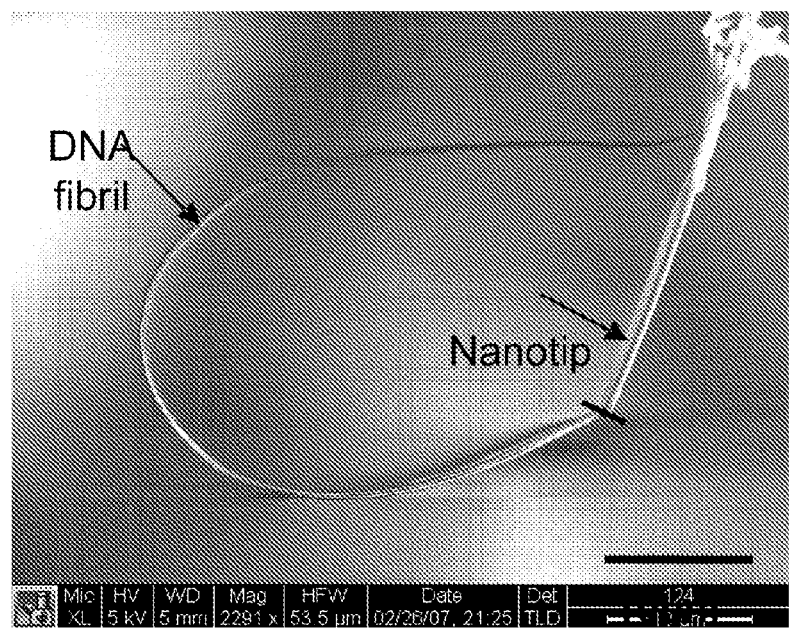

In this exemplary embodiment, DNA is captured on an electrode. λ-DNA in a TRIS EDTA (ethylenediaminetetraacetic acid) buffer solution was prepared. Using a CNT/SiC nanotip with an AC field, λ-DNA was concentrated on the electrode by dielectrophoresis and capillary action. FIGS. 6A-6C illustrate the captured λ-DNA molecules as a fibril on the nanotip.

By immersing and withdrawing a nanotip in a DNA solution (concentration: 500 μg/mL), a ~400 μm-long DNA fibril was formed at the end of the tip. Because many DNA molecules were present in the solution, the molecules formed the fibril by capillary force when the tip was withdrawn from the solution. FIG. 6A is an optical microscograph of the captured DNA on a nanotip, and FIG. 6B is the corresponding fluorescence microscograph (with the fluorescence resulting from DNA mixed with PICOGREEN® reagent). FIG. 6C is an electron micrograph of the sample of FIG. 6A.

An EDS (Energy Dispersive Spectroscopy) analysis (acceleration voltage: 10 kV) of the immobilized DNA identified elements including C, N, O, Na, Si, P, and Cl. C and Si arise from the SiC nanowires and CNTs. Na and Cl are present in the buffer solution. The elements of DNA, C, N, O, and P are also detected. Particularly P, which is an element unique to DNA in this system. Therefore, the fibril was confirmed as DNA. P was not detected in control samples not containing DNA.

Figure 6D:
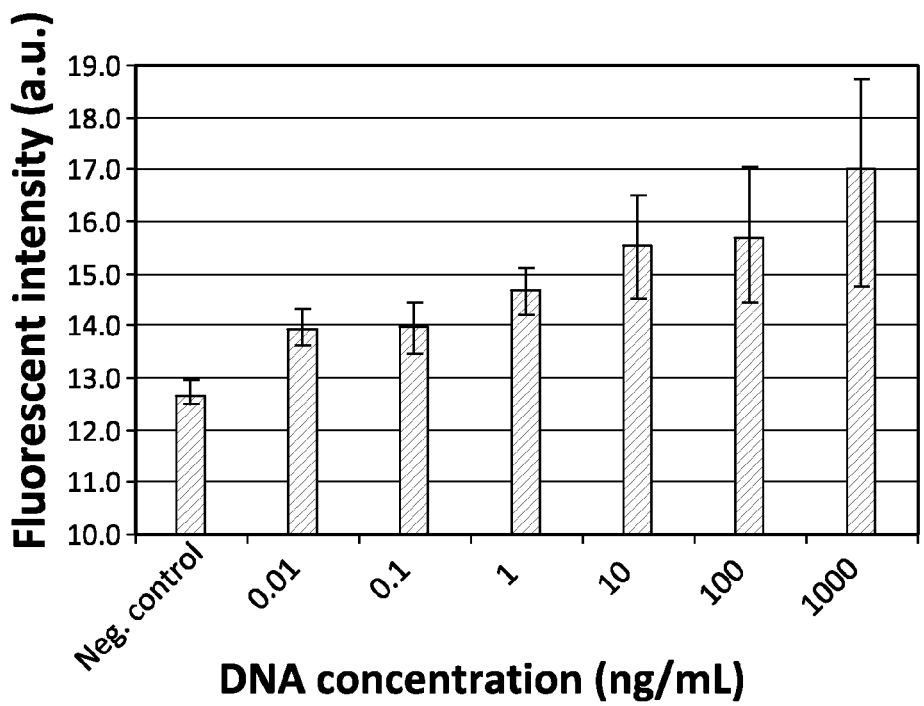
FIG. 6D is a graph of DNA concentration versus fluorescence intensity for a series of DNA solutions analyzed by the method of the invention.

DNA immobilization for pure and mixed samples was investigated. DNA molecules having various concentrations were immobilized on nanotips. The captured DNA was analyzed by fluorescence microscopy. The concentrations of DNA solutions were prepared from 1 pg/mL (32 aM) to 1 μg/mL (32 pM) by factors of 10. FIG. 6D is a graph of the fluorescence intensities measured using the method of the invention for different DNA concentrations. The experiment was repeated three times for each DNA concentration. The fluorescence intensities are compared with the negative control, measured with a pure PICOGREEN® reagent. The detection limit of the nanotip used in this experimental example is 10 pg/mL (320 aM).

Figure 7:
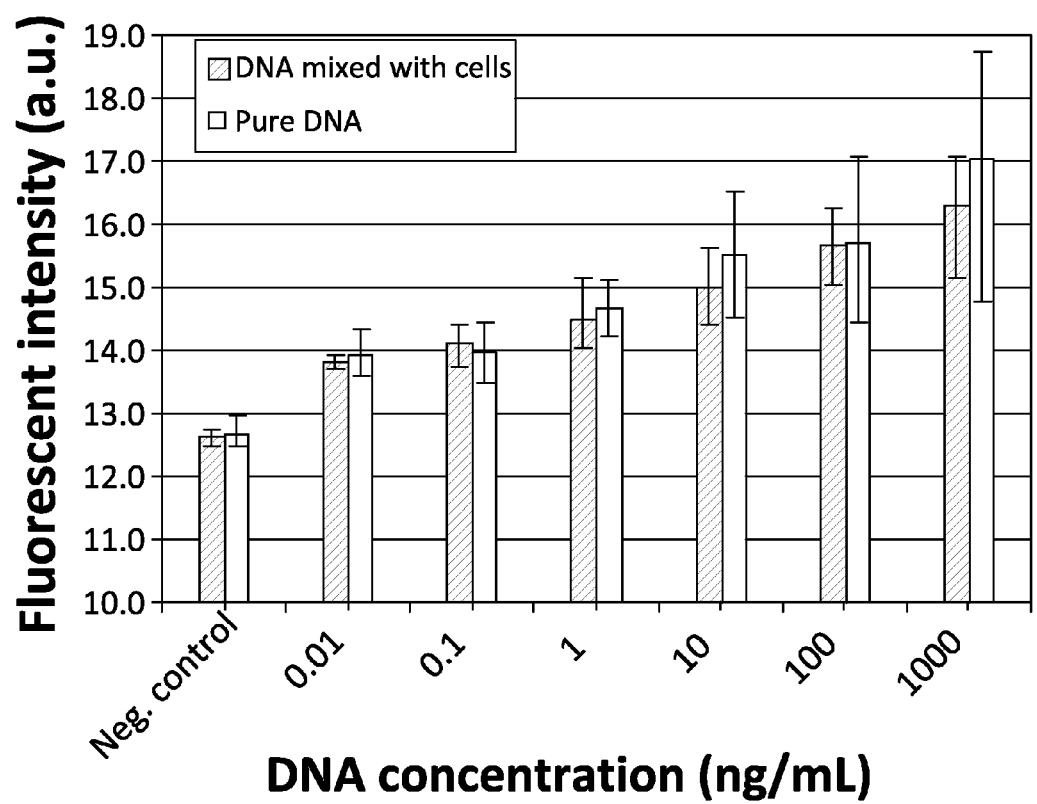
FIG. 7 is a graph of DNA concentration versus fluorescence intensity for a series of solutions of DNA and cells analyzed by the method of the invention.

To investigate the size-specific capturing of DNA from a sample mixture containing cells, *drosophila* cells were mixed with pure λ-DNA molecules in a TRIS EDTA buffer solution. The prepared DNA concentrations were from 0.67 pg/mL (21 aM) to 0.67 μg/mL (21 pM) by factors of 10. FIG. 7 is a graph comparing the detected fluorescence intensity of an electrode having immobilized DNA extracted from the DNA/cell mixture compared to a duplicate set of solutions containing DNA but no cells. The resulting intensity values indicate that the presence of cells in the DNA solution does not affect the accuracy of the method. DNA molecules were immobilized on the nanotip while cells remained in solution due to their larger size and the relatedly larger capillary force keeping them in the liquid. Because the normalized diameter of *drosophila* cells (10 μm) is much larger than the nanotip diameter (544 nm), the cells are not captured on the nanotip. In a follow-on experiment, however, the cells were immobilized on a microtip 250 μm in diameter using an AC potential (20 Vpp @ 5 MHz). The size specific capturing enables DNA detection in raw- or minimally-treated samples, and thus DNA can be detected without purification of samples, as is required for known DNA detection methods.

Free nucleic acids (e.g., circulating or dissolved DNA) can also be detected using the methods of the invention. Circulating DNA is of great interest in the fields of disease diagnostics and environmental molecular biology. Unlike the genomic DNA in normal cells, circulating DNA is free DNA released from dead cells. Thus, extracellular DNA circulating in body fluids can be used as an early indicator of various acute diseases, such as cancer. For example, the concentration of circulating DNA for a healthy person is ~30 ng/mL, but the concentration is increased up to ~300 ng/mL for a cancer patient.

For environmental monitoring, circulating DNA dissolved in lakes and soil is an indicator of environmental quality.

Despite its diagnostic potential, the study of circulating DNA is limited by standard sample preparation methods. The conventional techniques begin with filtering, centrifuging, and collecting DNA from a raw sample. In such protocols, genomic DNA is released and mixed with circulating DNA. Additionally, the slow sample preparation process can degrade and mutate circulating DNA. Therefore, a rapid process that can concentrate circulating DNA would be a beneficial diagnostic and analytical tool.

The methods of the invention provide for direct concentration and detection of free DNA. For example, a CNT/SiC nanotip electrode was used to immobilize free DNA from lake water. The experimental results indicate the capture of circulating dsDNA (double-stranded DNA) size-selectively while excluding cells or other larger particles that were observed in a raw solution using an optical microscope. Identification of the free DNA was by fluorescent tagging and microscopy.

Sequence-Specific Concentration of DNA Using Dielectrophoresis

In this exemplary embodiment, target DNA in a sample solution was delivered and concentrated on a CNT/SiC nanotip electrode with an induced dipole (DCP) moment under a high frequency AC field. The specific binding of the target DNA was achieved by sequence-specific hybridization to immobilized probe DNA. The final immobilization of DNA onto the nanotip was facilitated by capillary force during the withdrawal of the nanotip from the solution. The captured DNA was detected by fluorescence and/or electrical measurement.

Assuming that the target DNA in a spherical droplet 2 mm diameter is concentrated into a 1 μm$^3$ area of a nanotip terminal end, the concentration is by a factor of about $10^{10}$. Due to this dramatic concentration effect, the sensitivity of detecting DNA is enhanced by $10^6$ to $10^8$ times that of conventional non-enzymatic biosensors. Furthermore, DNA hybridization is accelerated by a high frequency AC field, which results in a detection time of 10 minutes compared to the hours or days required for known detection methods.

In this exemplary embodiment, the CNT/SiC nanotip was coated with polydimethylsiloxane (PDMS) to avoid nonspecific binding between DNA molecules and the CNTs of the nanotip. To investigate the sensitivity of a tip sensor, the AC field (5 MHz) and hybridization time were optimized, resulting in parameters of 10 Vpp and minutes, respectively. Probe DNA of *mycobacterium tuberculosis* (MTB) was prepared as 5'-Biotin-CAG CGC CGA CAG TCG GCG CTT GTG-3' (SEQ ID No. 1) (initial concentration: 38.3 µM, Invitrogen). The sequence includes codon 531 of MTB rpoB gene (wild type), which is regarded as a phylogenetic marker of TB, and also as a sensitive indicator of susceptibility to rifampin, one of the two common, first-line anti-tuberculosis drugs. The probe DNA was immobilized on the terminal end of the nanotip. The simulated target DNA was an oligonucleotide with the sequence 5'-CAC AAG CGC CGA CTG TCG GCG CTG-3' (SEQ ID No. 2) (initial concentration: 35.3 µM). An intercalating dye (PICOGREEN®, Invitrogen) was used to validate the hybridization through fluorescence. The target concentrations were controlled from 1 aM to 1 nM by 10-fold increments. The measured detection limit was 10 aM ($10^{-17}$ M, or 6,000 copies/mL), which is comparable to state-of-the-art detection methods, such as smear microscopy.

Bacteria Immobilization Using Electroosmotic Flow

Figure 8A:
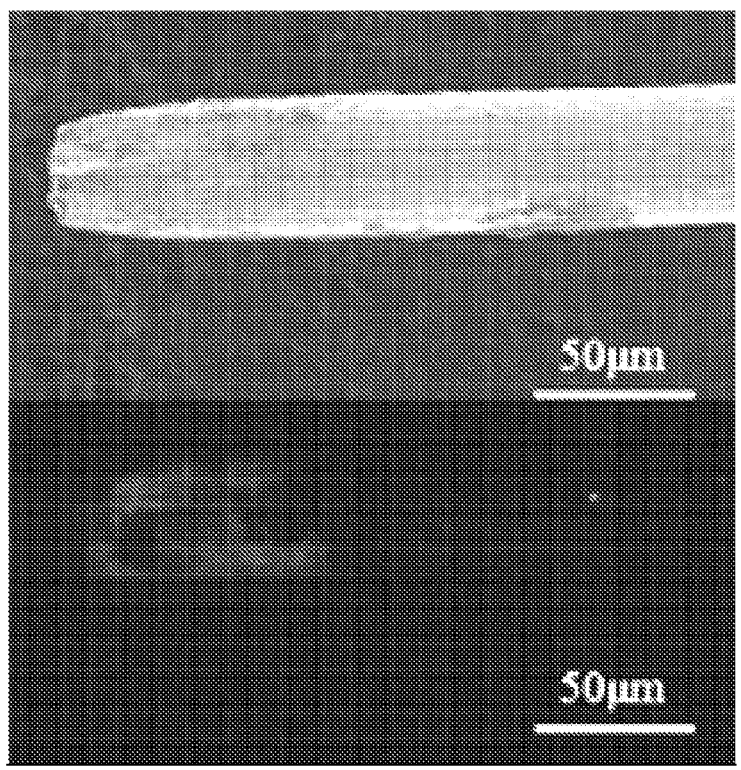
FIG. 8A is a micrograph of a first electrode having TB cells immobilized on its surface.

For culture-free detection of bacteria, a micron-scale electrode ("microtip") was used to immobilize and concentrate bacterial cells of *mycobacterium tuberculosis* (MTB). Bacteria in an aqueous solution were concentrated with the circulatory flow generated by an AC field (electroosmotic flow). The concentrated bacteria were attracted to the microtip surface by electroosmotic flow and an electrostatic attraction (electrophoresis). The final immobilization of attracted bacteria results from capillary force during withdrawal of the electrode from the liquid. FIG. 8A shows micrographs of a microtip having immobilized MTB cells on its surface under optical (top) and fluorescence (bottom) imaging.

The MTB was detected with a fluorescence microscope. For the fluorescence measurement, fluorescein-labeled polyclonal antibodies specific to the surface antigens of MTB were used (ViroStat Inc, Portland, Me.). The microtip having immobilized MTB cells was immersed in the antibody solution for five minutes and rinsed with deionized water. MTB cells were then detected under a fluorescence microscope (Olympus BX-41, Olympus America Inc., Melville, N.Y.).

Figure 8B:
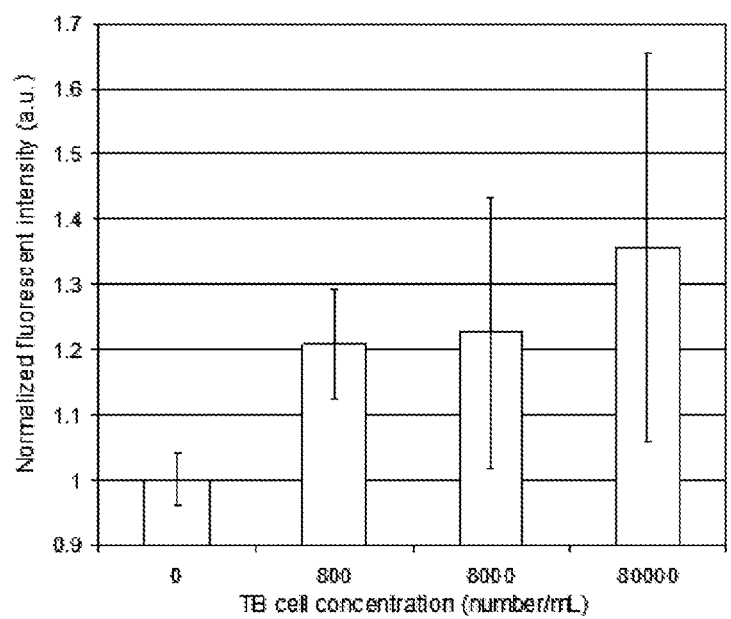
FIG. 8B is a graph of TB cell concentration versus fluorescence intensity for a series of solutions of TB analyzed by the method of the invention.

The sensitivity of the microtip sensor was at least 800 cells/mL, as illustrated in FIG. 8B. Detection was completed within 10 minutes. This bacterial concentration method can capture MTB bacteria from a raw biological sample, such as human sputum. To enhance the specificity of the capturing, antibodies can optionally be immobilized the electrode.

In a further experiment, the immobilized MTB bacteria are released into pure water (e.g., by immersion into boiling water) to extract their genomic DNA for species-specific detection with a nanotip, as described above with regard to DNA. Because the methods of the invention are non-enzymatic, and therefore not highly susceptible to interfering substances in lysates, DNA extraction can be accomplished by methods as rapid and simple as brief boiling in lysis/hybridization buffer and then performing the provided method of the invention using a nanotip to selectively capture the released DNA.

Electrical Detection of MTB Cells

Previous exemplary embodiments described above include detection of immobilized particles using optical and/or fluorescence detection. In this exemplary embodiment, electrical detection is utilized for MTB detection.

XYZ stages were used to precisely positionally control microtips of gold-coated tungsten for TB sensing and a similarly constructed reference sensor, both of which were immersed in a sample solution. The MTB sensor was used for capturing and detecting MTB while the reference sensor compensated for solution volume, distance between the electrodes, temperature, and ion concentrations in buffer. In an alternative embodiment, a microwell can be used that includes microelectrodes for reference sensing.

A 5 µL solution volume was used.

Figure 9A:
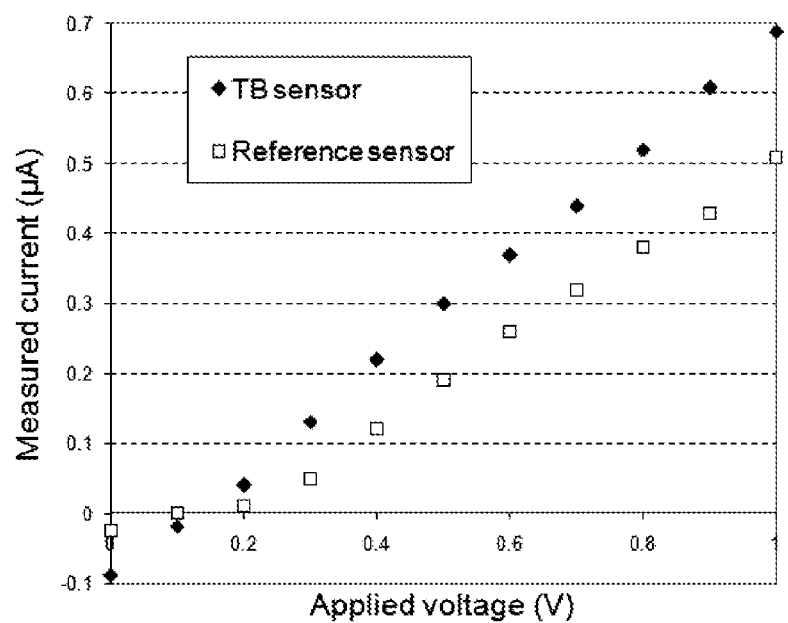
FIG. 9A is a graph comparing the applied voltage and measured current of a first electrode in a reference solution and in a solution containing TB.

FIG. 9A graphically illustrates a typical current-voltage curve for a system with an MTB sensor and a reference sensor. As the applied voltage increased, the measured current increased. Upon antibody-antigen reactions, the electrical resistance decreased. Compared to the electrical current of the reference sensor, the electrical current of the MTB sensor increased. The current difference between the MTB and the reference sensors is evaluated for detection of MTB.

To examine the performance of the sensor for a negative control, the microtip without MTB cells was immersed in an antibody solution for 5 minutes. Subsequently, the current was measured as a function of voltage. Currents were then measured for both the reference and the MTB sensor (sensing probe). For this electrical measurement, a tip having immobilized MTB cells was dipped into an antibody solution. The current was measured after 5 minutes, and was normalized by the current of the reference sensor. In three tests using three different pairs of microtips, the current ratio of the MTB sensors and the reference sensors $[(I_{TB}-I_{reference})/I_{reference}]$ showed 0.04±0.06 in average and standard deviation, respectively.

Figure 9B:
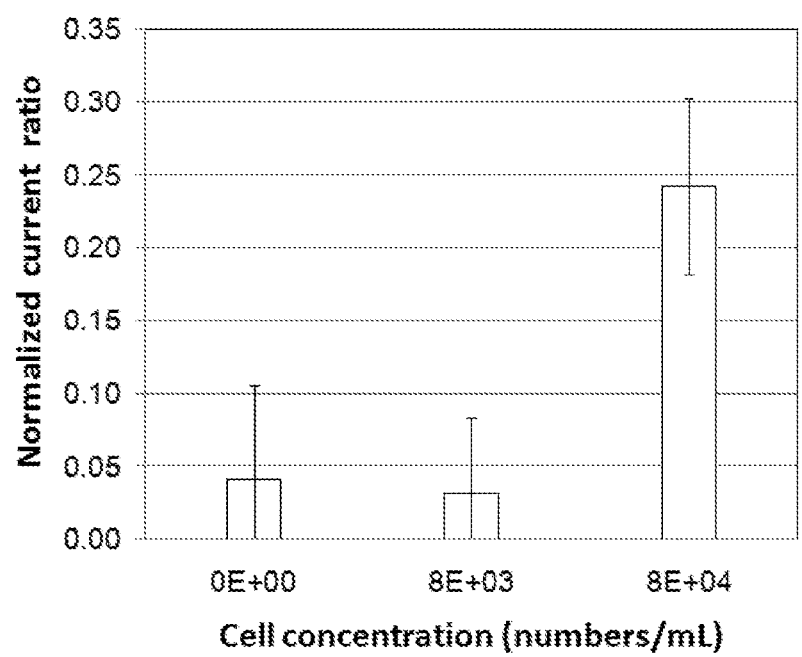
FIG. 9B is a graph of cell concentration of TB versus normalized current for a series of solutions containing TB analyzed by the method of the invention.

When the current ratios were measured for MTB concentrations of 0, $8 \times 10^3$, and $8 \times 10^4$ cells/mL, the current ratio rapidly increased at 80,000 cells/mL, as illustrated in FIG. 9B.

Electrical DNA Detection Using a Single Electrode

The above exemplary embodiment utilizes two electrodes, a probe electrode and a reference electrode, to detect bacteria in an antibody/antigen reaction. In this exemplary embodiment, a single electrode is used for electrical detection of particles. The target particles include metallic particles to improve detection sensitivity.

For example, a CNT/SiC nanotip coated with amine-doped SWCNTs or metallic-SWCNTs improves sensitivity of detecting particles labeled with metallic particles. The band gap of the amine-doped SWCNTs rapidly changes upon DNA binding.

Metallic-SWCNTs improve the signal to noise ratio of the device because the contact resistance between the SWCNTs and metallic electrode is reduced compared to non-metallic SWCNT.

Figure 10:
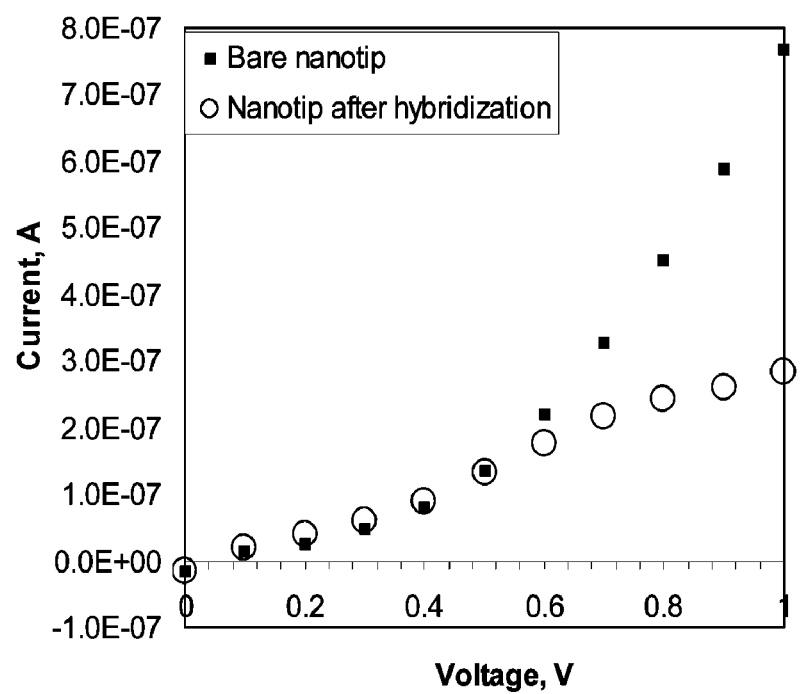
FIG. 10 is a graph of voltage versus current for a first electrode having DNA hybridized on its surface and a reference first electrode with no DNA.

For hybridization experiments, the change of resistance ($R_f$) and capacitance ($C_{dl}$) are measured after immobilization of particles on the electrode. The variation of $C_{dl}$ is ascribed to electrical double layer effects on a electrode, while the change of $R_f$ is due to DNA hybridization. The change of the values is monitored such that the sensitivity of a nanotip electrode to hybridization events can be determined. Once the signal analysis is completed with a square signal, an I-V (shown in FIG. 10) or continuous-DC analyzing is performed to detect the events, which can then be compared to fluorescence measurements for confirmation.

Enhancement of Reactions on an Electrode Using an Electric Field

By applying an electric field to the electrode, biological and chemical reactions can be accelerated due to the orientation of molecules on the surface of the electrode (e.g., first binding partners) and their attraction of second binding partners attached to particles. The acceleration of DNA hybridization using the methods of the invention is described below.

A CNT/SiC nanotip electrode was coated with PDMS, which was then coated with streptavidin as a binding partner for DNA. Target DNA (1 pM, 1.5 µL) was hybridized for 5 minutes using AC potentials applied to the electrode at 0, 5, and 10 Vpp. Voltage greater than 10 Vpp was not applied due to electrical break down at such voltages. After hybridization, intercalating dye was used to investigate the hybridization of DNA with fluorescence spectroscopy. The fluorescence intensity was used to determine the change of the hybridization upon the application of an AC field.

Figure 11A:
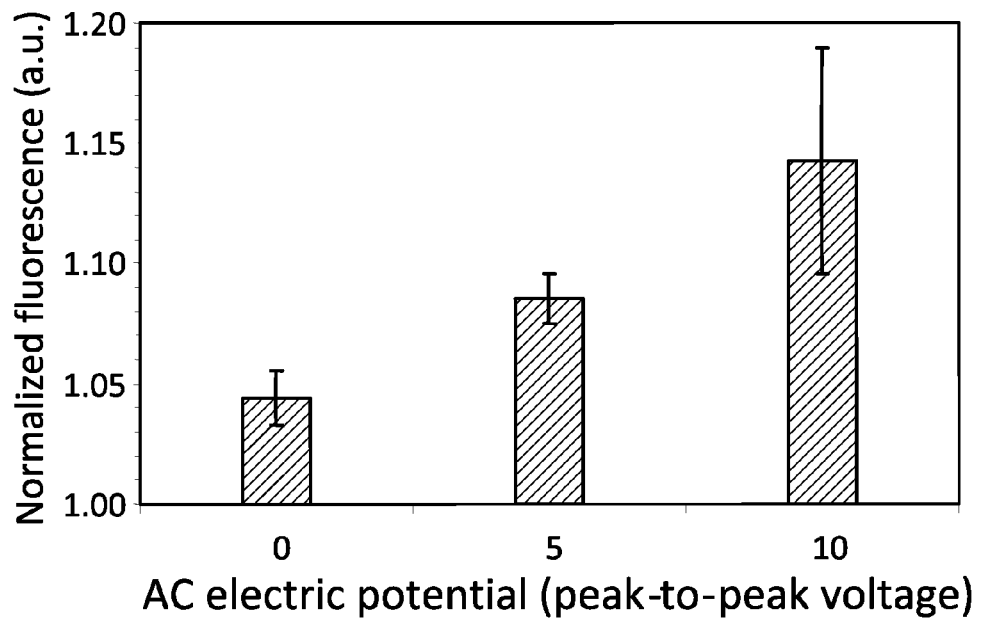
FIG. 11A is a graph of AC voltage versus fluorescence for DNA hybridization using the methods of the invention.

FIG. 11A shows the fluorescence intensity of DNA immobilized at different AC potentials. As the AC potential increases, the intensity increases due to higher concentration of DNA on the electrode. 10 Vpp provided the largest enhancement of DNA hybridization.

Figure 11B:
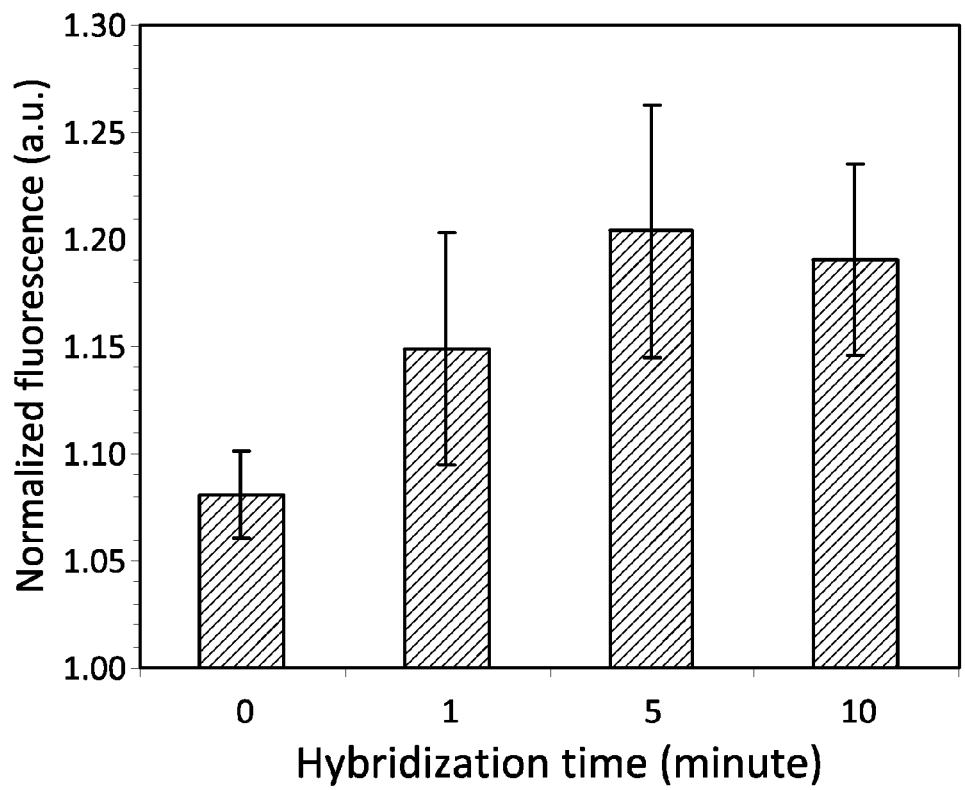
FIG. 11B is a graph of DNA hybridization time versus fluorescence for DNA hybridization using the method of the invention.

Hybridization time was also investigated. The fluorescence intensity was measured at various hybridization times under 10 Vpp. The fluorescence intensity saturated when the hybridization time was greater than 5 minutes, as illustrated in FIG. 11B.

Thus, for the above system, the optimal AC potential and the hybridization time were determined to be 10 Vpp and 5 minutes, respectively.

Immobilization of HIV-B Viruses and RNA Detection

In this exemplary embodiment, an electrode is used to immobilize a virus (HIV-B). Subsequent to immobilization of the virus, RNA from the virus is detected using fluorescence spectroscopy.

A CNT/SiC nanotip (diameter 500 nm) was used as an electrode. An HIV-B virus solution was Armored RNA Quant HIV-B kit (Asuragen, Inc, Austin, Tex.) at a concentration of 50,000 copies/mL. For RNA detection, a Quant-iT RiboGreen RNA reagent in DMSO was used, wherein the fluorescence excitation/emission was 500/525 nm when bound to nucleic acid. The reagent was diluted 200× (from the as-purchased concentration) for RNA detection.

Figure 12:
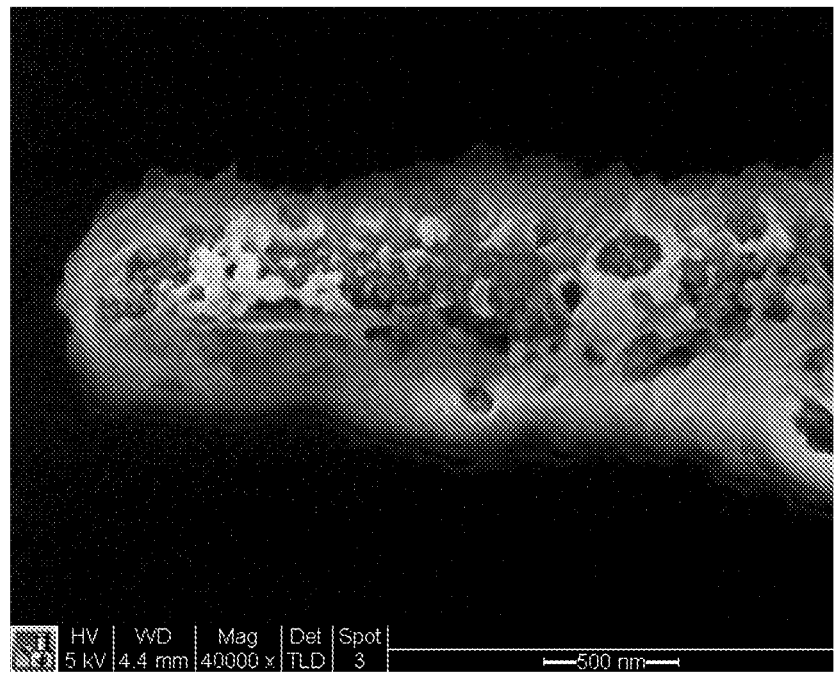
FIG. 12 is a micrograph of a first electrode having HIV immobilized on its surface by the method of the invention.

The nanotip (first electrode) was immersed in a 20 µL droplet of the virus solution suspended in a metallic coil (second electrode). A 14 Vpp, 5 MHz signal was applied across the electrodes for one minute to immobilize the HIV on the nanotip. The nanotip was then withdrawn at about 10 µm/sec to further immobilize the HIV. The immobilized HIV on the nanotip was then imaged using SEM, as illustrated in FIG. 12.

Figure 13A:
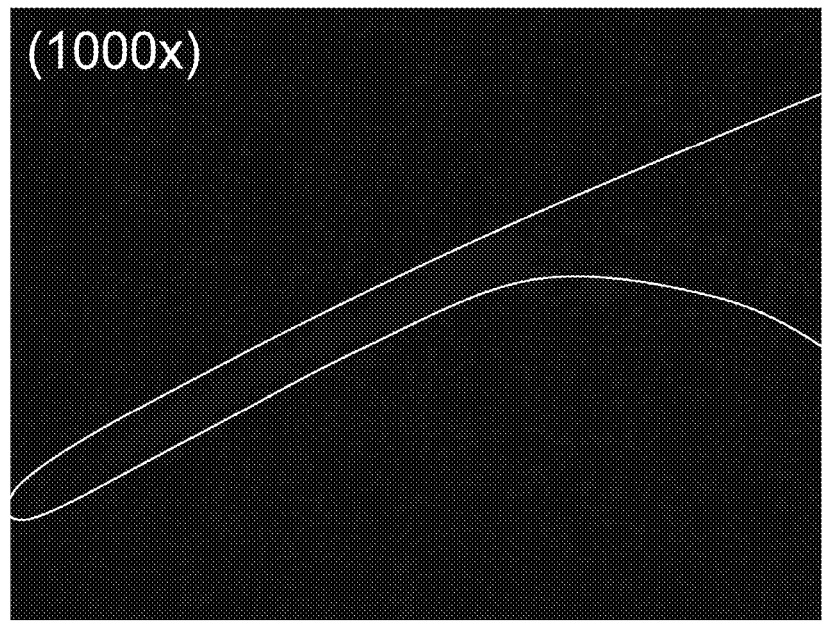
FIG. 13A is a fluorescence micrograph of a first electrode prior to its use in the method of the invention.
Figure 13B:
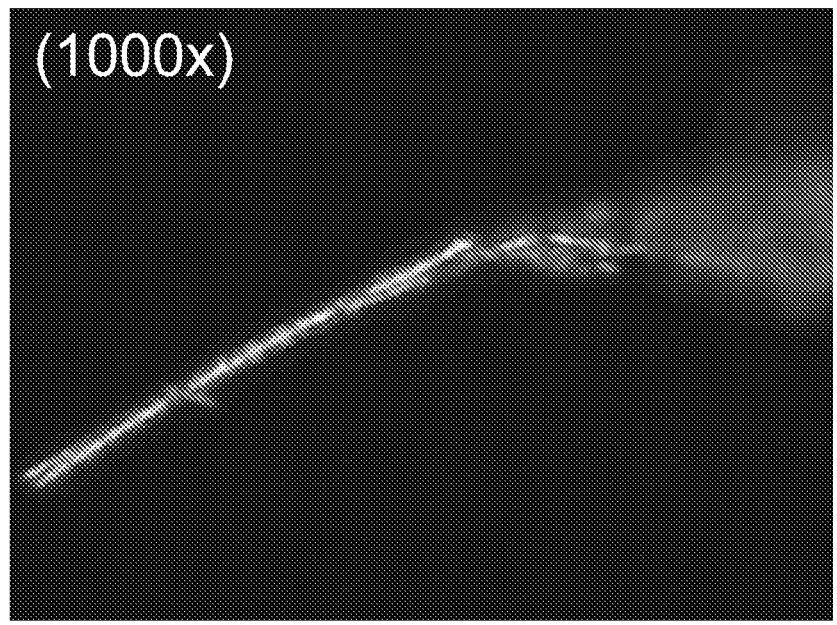
FIG. 13B is a fluorescence micrograph of the first electrode pictured in FIG. 13A subsequent to the method of the invention whereby HIV was immobilized on the surface of the electrode.

Immobilized HIV on the nanotip was further used to test for RNA. The nanotip having immobilized HIV was immersed in a 2 uL droplet of RIBOGREEN reagent for five minutes without an electric field, during which time the RIBOGREEN was inserted into the RNA inside the virus. The nanotip was then removed from the solution and analyzed by fluorescence microscopy. FIG. 13A is a fluorescence micrograph of the nanotip having HIV-B immobilized on its surface prior to immersing in the RIBOGREEN solution. The white line is provided to illustrate the location of the nanotip in the micrograph. FIG. 13B is a fluorescence micrograph of the nanotip after treatment with RIBOGREEN. The RNA within the HIV-B immobilized on the nanotip fluoresces after treatment with RIBOGREEN.

Thus, both viruses and the RNA contained within viruses can be immobilized and detected using the methods of the invention.

Detection of Nucleic Acids in Immobilized Cells

In this exemplary embodiment, in-situ hybridization (ISH) is described. The use of fluorescent probes to detect nucleic acids within cells is know in the prior art. This technique is regarded as a powerful analytical tool for investigating cells (e.g. detecting rRNA or mRNA in bacterial cells as an indicator of viable bacteria) and viruses (e.g. detecting RNA or DNA in viral particles) directly. However, known ISH methods suffer from both limited sensitivity and the difficulty of fixing cells onto a solid support, as required for known methods.

The embodiment described herein utilizes an electrode (e.g., nanotip or microtip) for immobilizing cells for ISH analysis. In the method, cells are immobilized on a microtip (first electrode) and then subsequently immersed in a second solution containing nucleic acid probes that allow for detection of cellular nucleic acids within the cell. The in situ detection of nucleic acids in cells allows for improved detection time and minimal processing to achieve sensitive detection of cellular nucleic acids.

First, cells were immobilized on a microtip using the methods of the invention, and, optionally, with a functionalized microtip to specifically bind the cells to the microtip. The immobilized cells were immersed in a second solution containing nucleic acid probes with a sequence matching a specific region of genetic nucleic acids within the cells. The probes permeated the immobilized cells and hybridized to the matching genetic regions within the cells. Upon hybridization, a detectable moiety (e.g., a fluorescent moiety) was formed such that the hybridized nucleic acids were detected.

Purification of Heterogeneous Particle Solutions

The methods of the invention can be used to purify heterogeneous solutions of particles (e.g., particles of different size and/or composition). Size selective immobilization of particles on an electrode is performed according to the methods described herein. If, for example, the immobilized particles comprise a mixture of DNA and a protein, the immobilized particles can be immersed in a second solution and released from the electrode. The second solution with the DNA and proteins is then filtered (e.g., with filter paper or chromatography). If the proteins are filtered out of the second solution, then DNA remains in the second solution. The DNA can then be recaptured by immobilizing on an electrode according to the provided methods.

Thus, a complex mixture (e.g., a biological fluid), can be purified using the methods described herein. Any mixture of particles described herein can be separated using the methods provided.

Manipulating Bacteria, Cells, and Other Particles

The methods of the invention can be used for molecular engineering. Particularly, immobilized molecules on a nanotip can be used for manipulating the properties of bioparticles and other molecules for molecular design; nanomanufacturing; and precision control.

In one embodiment, the immobilized molecules are positioned within a bioparticle, for example, a bacteria. As a result, individual bacteria (viruses) are used as biochemical laboratories confined by the cell membrane. In such a system, DNA is amplified with chemical energy, and proteins can be tested and detected for biocompatibility and antibiotics. Such an autonomous "molecular foundry" is enabled by the methods of the invention In the provided molecular foundry, nucleic acids and/or proteins can be captured and released in a specific way by use of an energy selected from electrical, thermal, mechanical, and chemical energy. The particles inserted from a nanotip into bacteria or viruses can be used as a disease indicator (sensor), for drug delivery (therapeutics), for genetic modification, and for genetic engineering.

Format of Devices

The method of the invention can be practiced on any number of devices. For example, one exemplary device includes a fully automated device having an array of electrodes with optical and electrical detection units, as well as control units for all aspects of the device.

A fully automated device can be used for multiplexing pathogens and various analytes.

In one exemplary embodiment, the device for performing the method includes a portable concentrator, which includes an electronic unit for analysis and a tip electrode. Such a device may be highly portable and disposable, such as a device formed to have a pen shape with a manual "clicking" function for actuating the tip to immerse and withdraw the electrode from a sample solution.

Analysis of the Mechanism for Particle Immobilization

Figure 14:
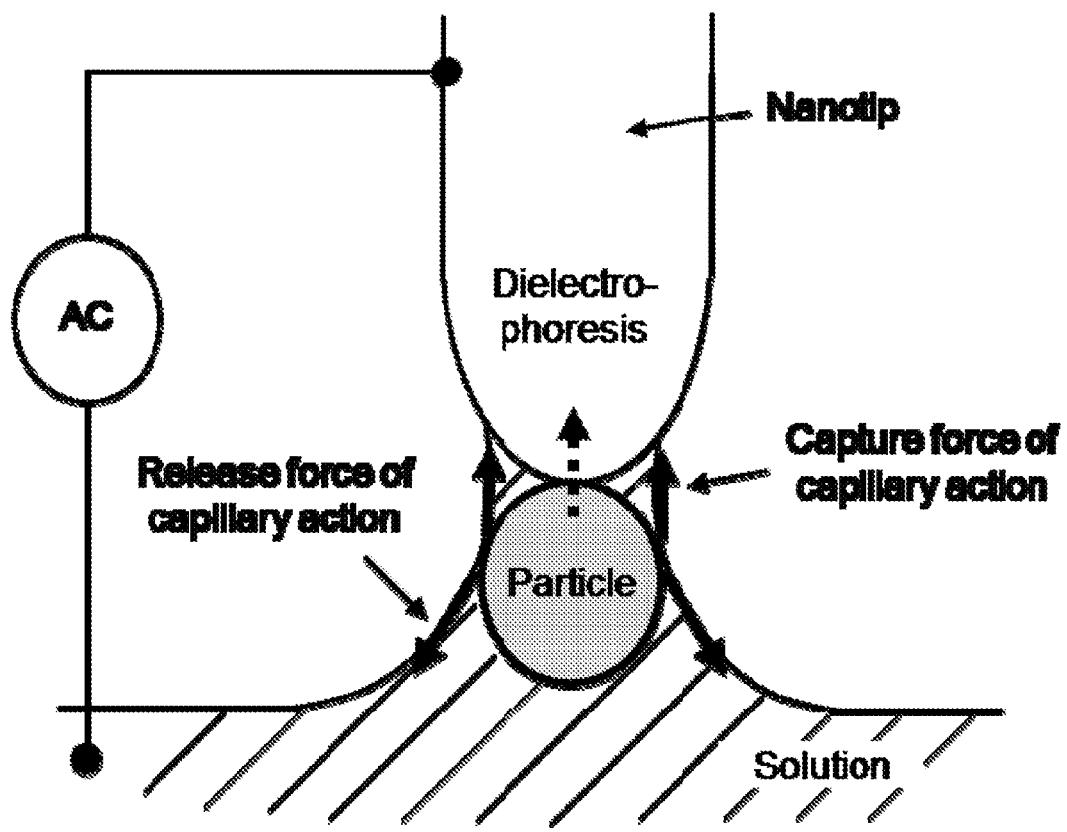
FIG. 14 is a diagrammatic illustration of the forces acting on a particle immobilized on an electrode in accordance with the present invention.

FIG. 14 illustrates a particle immobilization process using an AC electric field and capillary action. To capture the particle, a nanotip electrode is immersed in a solution with an AC field applied across the nanotip electrode and a second electrode in contact with the solution. The inhomogeneous electric field generated by the electrodes results in polarization of the particle and attraction of the particle to the nanotip by DEP. When the tip is withdrawn from the solution, the attracted particle can be captured or released on the tip based on the combined effects of capillary action and DEP force. The DEP force attracts particles to the tip while the capillary forces can capture or release particles on the tip. To predict the capturing process of particles, the capture and release forces due to capillary action are examined below.

Figure 15A:
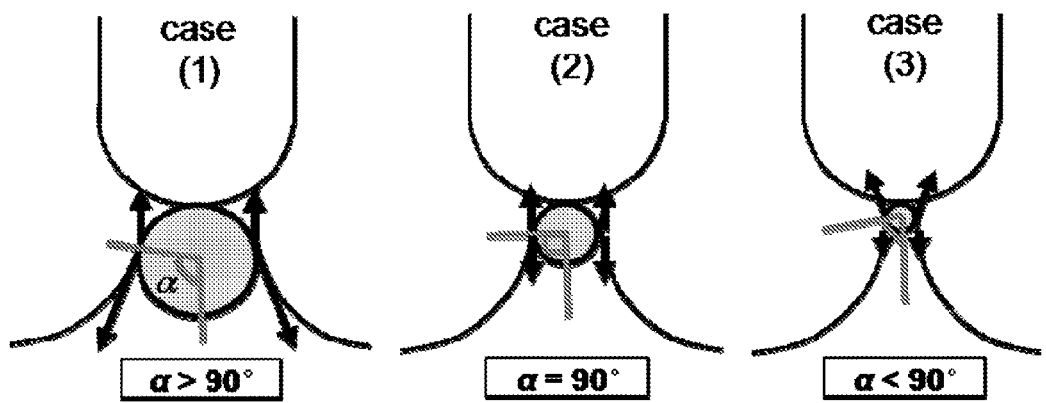
FIG. 15A is a diagrammatic illustration of the critical angles formed between a liquid and different sized particles as the particles are immobilized on an electrode withdrawing from the liquid.

To determine the capillary forces acting on a sphere, capturing and releasing forces due to capillary action were analyzed using the meniscus profiles generated by the Young-Laplace equation. FIG. 15A illustrates the mechanism of size-specific capturing. Depending on the diameter ratios of a particle to the tip, the particle can be captured or released from the tip. The capturing is determined by the split angle α because capillary forces for the capturing and releasing depend on the circumference at the split point. At the split point, the solution is separated into the upper and lower parts. When the split angle is greater than 90°, the particle stays in the solution (case (1) in FIG. 15A). The particle is captured onto the tip (case (3) in FIG. 15A) when the split angle is smaller than 90°. At a split angle of exactly 90° (case (2) in FIG. 15A), the capture of a particle is not determined because the capillary forces acting toward the tip and the solution are equal.

Figure 15B:
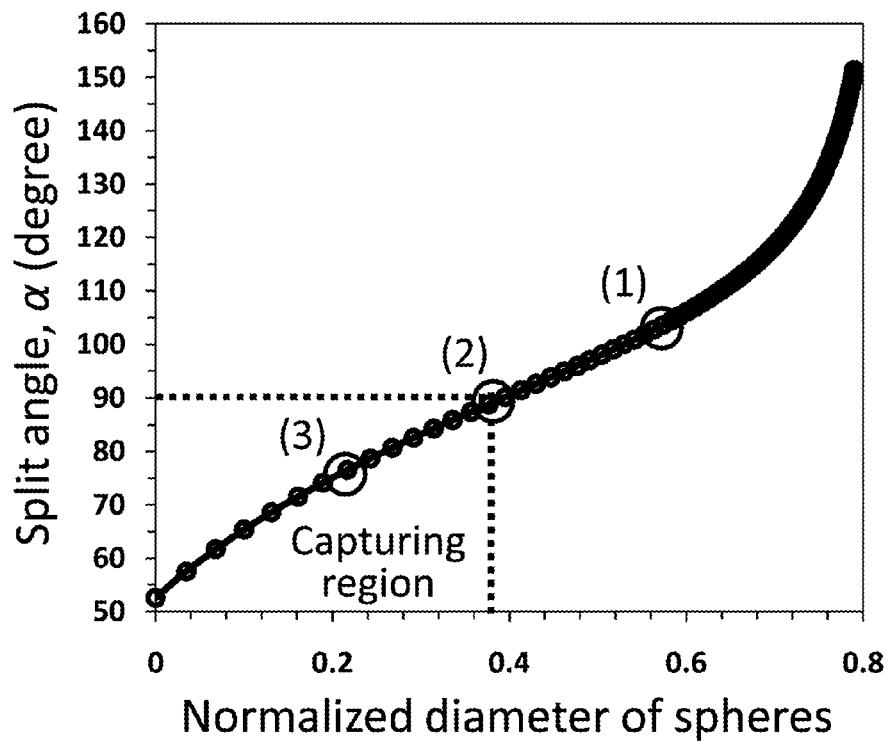
FIG. 15B is a graph of the split angle formed between a liquid and different sized particles as the particles are immobilized on an electrode withdrawing from the liquid.

A critical normalized diameter [$(d_n)_{critical}$] is defined as the normalized diameter at the split angle of 90°. The $(d_n)_{critical}$ in the configuration of case (2) in FIG. 15A is estimated by the numerical analysis to be 0.39, as shown in FIG. 15B. By this theoretical analysis, as long as the ratio of the particle diameter ($d_p$) to the tip diameter ($d_t$) is less than 0.39, the particle is captured onto the tip. The $(d_n)_{critical}$ can be changed by (1) surface-interaction energy selected from electrical, chemical, mechanical, and thermal energy, (2) tip shape and particle morphology, and (3) particle-particle interactions (e.g. colony formation of cells).

In the above comparison of capillary forces, electrical forces (e.g., DEP) were not considered when calculating $(d_n)_{critical}$. For example, if DEP is included in this calculation, the $(d_n)_{critical}$ will be increased because the DEP force is added to the capturing capillary force. In addition, the $(d_n)_{critical}$ affected by the experimental conditions including the tip geometry, the multiple particle interaction, and the contact angles of the particle and tip with the liquid.

Table 1 summarizes immobilization results for polystyrene spheres and CNT/SiC nanotips. The largest sphere diameter captured by the tip is normalized by the tip diameter in order to obtain $(d_n)_{critical}$. According to Table 1, the $(d_n)_{critical}$ is in the range of 0.84±0.07 (average±standard deviation) using the cases (2), (3), (4), and (5).

In this way, the $(d_n)_{critical}$ using the polystyrene nanospheres was determined in the range of 0.77~0.92 (0.84±0.07). In the mixture experiment of 100 nm and 6 μm spheres discussed above with regard to FIG. 5C, 6 μm spheres were not immobilized on a nanotip because the $(d_n)_{ave}$ of the 6 μm spheres was much greater than the range of $(d_n)_{critical}$.

TABLE 1

Size-specific immobilization of polystyrene spheres on an electrode

| | $d_{nanotip}$ (nm) | $d_{sphere}$ | $(d_n)_{ave} = d_{sphere}/d_{nanotip}$ | $(d_{capture})_{max}$ | $(d_n)_{critical} = (d_{capture})_{max}/d_{nanotip}$ | Immobilized Particles? |
|---|---|---|---|---|---|---|
| (1) | 360 | 100 nm | 0.28 | 125 nm | NA | Yes |
| (2) | 595 | 490 nm | 0.82 | 461 nm | 0.77 | Yes |
| (3) | 347 | 300 nm | 0.86 | 274 nm | 0.79 | Yes |
| (4) | 526 | 490 nm | 0.93 | 451 nm | 0.86 | Yes |
| (5) | 514 | 490 nm | 0.95 | 475 nm | 0.92 | Yes |
| (6) | 623 | 700 nm | 1.12 | NA | NA | No |
| (7) | 773 | 950 nm | 1.22 | NA | NA | No |

$d_{nanotip}$: nanotip diameter, $d_{sphere}$: nominal diameter of nanospheres from the vendor's information, $(d_n)_{ave}$: averaged normalized diameter ($d_{sphere}/d_{nanotip}$), $(d_{capture})_{max}$: maximum diameter of captured spheres, $(d_n)_{critical}$: critical normalized diameter [$(d_{capture})_{max}/d_{nanotip}$], and 'NA' means 'not applicable'.

Comparing the $(d_n)_{critical}$ (0.84±0.07) of the experimental results to the $(d_n)_{critical}$ (0.39) of the theoretical analysis discussed above, the experimental $(d_n)_{critical}$ is higher than the theoretical $(d_n)_{critical}$. This discrepancy is attributed to the DEP force generated from the AC field. Because the DEP force is added to the capturing capillary force, the $(d_n)_{critical}$ is increased. The use of binding partners attached to the electrode and particle can further increase the $(d_n)_{critical}$. In one embodiment, the particle has a critical dimension (e.g., $(d_n)_{critical}$) larger than the latitudinal dimension of the first electrode. In one embodiment, the particle has a critical dimension (e.g., $(d_n)_{critical}$) smaller than the latitudinal dimension of the first electrode.

Figure 16A:
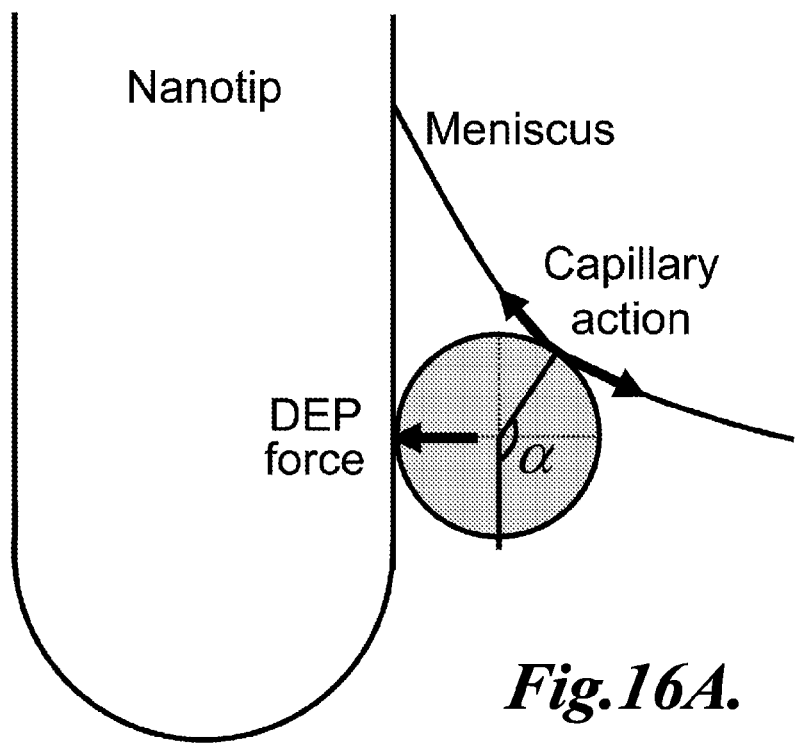
FIG. 16A is a diagrammatic illustration of the forces acting on a particle immobilized on an electrode withdrawing from a liquid.

As illustrated in the micrograph of FIG. 5A and diagrammatically in FIG. 16A, the DEP force attracts spheres to the side of a tip. Without the DEP force, the spheres are attracted primarily to the tip end because the split angle (α) in FIG. 16A is always greater than 90°.

In addition to the DEP force, the discrepancy of the $(d_n)_{critical}$ between the theoretical and experimental results is caused by additional experimental conditions, including tip geometry, multiple-particle interactions, and contact angles.

A sphere at the side of a tip may not be pulled to the end of the tip if the surface of the nanotip is rough or the orientation of the nanotip is not exactly orthogonal to the tangent of a spherical drop during the withdrawal of a tip. In this case, a split angle smaller than 90° can be instantly generated, and thus, the sphere can be captured onto the side of a tip. On the side of a tip, particles can also be immobilized by electrostatic attraction, chemical binding energy, and nonspecific molecular interactions.

Figure 16B:
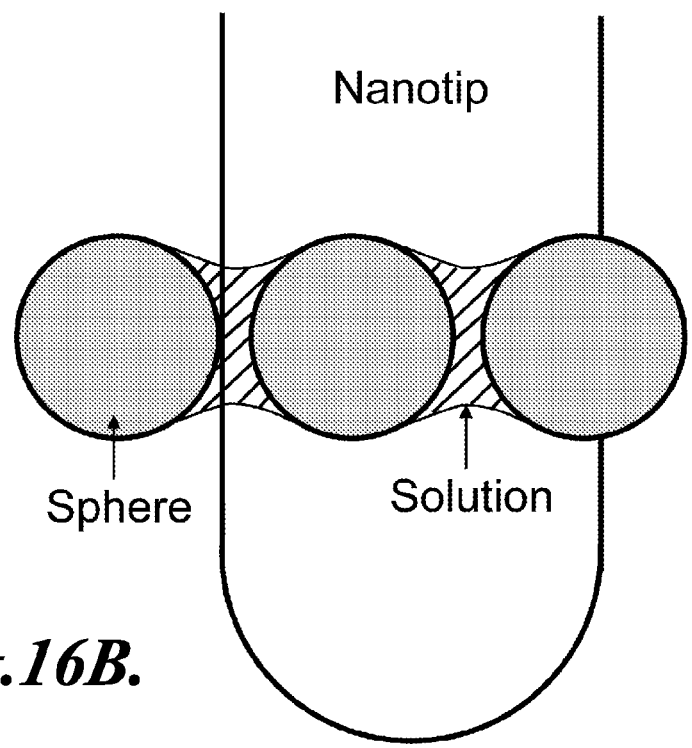
FIG. 16B is a diagrammatic illustration of multiple particles immobilized on the side of an electrode.

When a tip is surrounded with a cluster of spheres, the spheres are captured onto the side of the tip by a multiple-particle interaction force, as shown in FIG. 5B. The cluster formation around a tip is frequently observed during the immobilization process because the spheres are delivered to the solid-liquid-gas interface by capillary action. The delivery of particles to the interface can be generated by the DEP force in conjunction with evaporation of a solution and the compressive force due to capillary action. As evaporation continues, the capillary action among the attracted spheres can generate a coagulating force, as illustrated diagrammatically in FIG. 16B. Therefore, the interactive forces among the delivered spheres can increase the capturing force.

Other than the geometric- and the multiple-particle interaction effects, the $(d_n)_{critical}$ can vary due to the contact angle of tip surface. The contact angle of the tip can be changed by changing the surface properties of a tip, the hysteresis, and an electric field (e.g. electro-wetting). Also, molecular interaction forces (e.g. van der Waals force) can affect $(d_n)_{critical}$. Therefore, $(d_n)_{critical}$ can be modified by the specific experimental conditions to selectively immobilize the desired particles from a liquid.

While illustrative embodiments have been illustrated and described, it will be appreciated that various changes can be made therein without departing from the spirit and scope of the invention.

2. The method of claim 1 further comprising analyzing the nucleic acid immobilized on the surface of the first electrode.

3. The method of claim 2, wherein analyzing the nucleic acid comprises a method selected from the group consisting of electrical, mechanical, optical, surface-imaging techniques, and combinations thereof.

4. The method of claim 3, wherein analyzing the nucleic acid by an optical method comprises attaching a luminescent compound to the nucleic acid to provide a luminescent particle and detecting luminescence from the luminescent particle.

5. The method of claim 3, wherein analyzing the nucleic acid by an electrical method comprises a technique for measuring a characteristic selected from the group consisting of capacitance, resistance, conductance, impedance, and combinations thereof.

6. The method of claim 1, wherein the first electrode comprises a material selected from the group consisting of a metal, a doped semiconductor, and a conductive polymer.

7. The method of claim 1, wherein the latitudinal dimension of the first electrode is larger than a longitudinal dimension of the nucleic acid.

8. The method of claim 1, wherein the first electrode is at least partially coated with a surface coating.

The invention claimed is:

1. A method for concentrating a nucleic acid, comprising:

(a) immersing a first electrode having a high aspect ratio in a liquid comprising a nucleic acid, wherein the first electrode comprises a shaft having a shaft latitudinal dimension and a distal end having a distal latitudinal dimension, wherein the distal latitudinal dimension is from one nanometer to one millimeter;

(b) urging the nucleic acid toward the first electrode by generating an electric-field-induced force using the first electrode; and (c) immobilizing the nucleic acid on a surface of the first electrode with a capillary force formed between the first electrode and the liquid by withdrawing the first electrode from the liquid;

wherein the electric-field-induced force is created by an electric field that is maintained through the step of immobilizing the nucleic acid on a surface of the first electrode with a capillary force formed between the first electrode and the liquid by withdrawing the first electrode from the liquid.

9. The method of claim 8, wherein the surface coating is selected from the group consisting of a monolayer and a polymer layer.

10. The method of claim 8, wherein the surface coating enhances the immobilization of the nucleic acid on the first electrode.

11. The method of claim 10, wherein the surface coating comprises a first binding partner and the nucleic acid comprises a second binding partner capable of binding to the first binding partner.

12. The method of claim 11, wherein the first binding partner is a first nucleic acid.

13. The method of claim 11, wherein the first binding partner is a protein.

14. The method of claim 1, wherein the electric-field-induced force is selected from the group consisting of electrophoresis, electroosmosis, dielectrophoresis, and combinations thereof.

15. The method of claim 1, wherein the electric-field-induced force is generated between the first electrode and a second electrode in contact with the liquid.

16. The method of claim 1, wherein the liquid is selected from the group consisting of a solution and a suspension.

17. The method of claim 1, wherein the liquid is a biological fluid selected from the group consisting of blood, sputum, mucous, and saliva.

18. The method of claim 1, wherein the nucleic acid is DNA or RNA.

* * * * *